US005550189A

United States Patent [19]
Qin et al.

[11] Patent Number: 5,550,189
[45] Date of Patent: Aug. 27, 1996

[54] MODIFIED POLYSACCHARIDES HAVING IMPROVED ABSORBENT PROPERTIES AND PROCESS FOR THE PREPARATION THEREOF

[75] Inventors: Jian Qin; James R. Gross, both of Appleton; William J. Mui, Neenah; Xin Ning; Wen Z. Schroeder, both of Appleton; Tong Sun, Neenah, all of Wis.

[73] Assignee: Kimberly-Clark Corporation, Neenah, Wis.

[21] Appl. No.: 145,453

[22] Filed: Oct. 29, 1993

Related U.S. Application Data

[63] Continuation-in-part of Ser. No. 870,529, Apr. 17, 1992, abandoned.

[51] Int. Cl.$^6$ ............................................. C08F 8/00
[52] U.S. Cl. ..................... 525/54.3; 525/54.31; 527/300; 536/124
[58] Field of Search ................. 536/112, 124, 536/120; 525/54.3, 54.31; 527/300, 310, 312

[56] References Cited

U.S. PATENT DOCUMENTS

| | | | |
|---|---|---|---|
| Re. 30,029 | 6/1979 | Smith | 128/285 |
| Re. 31,323 | 7/1983 | Marder et al. | 536/87 |
| 1,682,294 | 8/1928 | Lilienfeld . | |
| 1,884,629 | 10/1932 | Dreyfus . | |
| 1,938,360 | 12/1933 | Traill . | |
| 2,096,681 | 10/1937 | Lorand . | |
| 2,110,526 | 3/1938 | Lorand . | |
| 2,131,733 | 10/1938 | Haskins et al. . | |
| 2,137,343 | 11/1938 | Maxwell . | |
| 2,159,376 | 5/1939 | Freeman et al. . | |
| 2,170,009 | 8/1939 | Clarke et al. . | |
| 2,181,264 | 11/1939 | Dreyfus . | |
| 2,236,523 | 4/1941 | Coolidge . | |
| 2,236,545 | 4/1941 | Maxwell et al. . | |
| 2,278,612 | 4/1942 | Collings et al. . | |
| 2,486,805 | 11/1949 | Seymour et al. | 117/68 |
| 2,517,577 | 8/1950 | Klug et al. . | |
| 2,523,377 | 9/1950 | Klug . | |
| 2,524,024 | 9/1950 | Swinehart et al. . | |
| 2,639,239 | 5/1953 | Elliott | 106/197 |
| 2,680,737 | 6/1954 | Grassie et al. . | |
| 2,772,999 | 12/1956 | Masci et al. | 167/84 |
| 2,773,000 | 12/1956 | Masci et al. | 167/84 |
| 2,976,278 | 3/1961 | Paddison et al. . | |
| 3,055,369 | 9/1962 | Graham, Jr. | 128/285 |
| 3,229,769 | 1/1966 | Bashaw et al. | 169/1 |
| 3,339,550 | 9/1967 | Van Haaften | 128/290 |
| 3,345,358 | 10/1967 | Inklaar . | |
| 3,347,236 | 10/1967 | Torr | 128/284 |
| 3,347,855 | 10/1967 | Nelson . | |
| 3,379,720 | 4/1968 | Reid . | |
| 3,423,167 | 1/1969 | Kuzmak et al. | 8/129 |
| 3,551,410 | 12/1970 | MacDonald et al. . | |
| 3,589,364 | 6/1971 | Dean et al. | 128/284 |
| 3,618,607 | 11/1971 | Ells et al. | 128/285 |
| 3,678,031 | 7/1972 | Schoggen . | |
| 3,723,413 | 3/1973 | Chatterjee et al. . | |
| 3,731,686 | 5/1973 | Chatterjee | 128/285 |
| 3,826,711 | 7/1974 | Schoggen et al. | 162/102 |
| 3,847,636 | 11/1974 | Smith | 106/168 |
| 3,858,585 | 1/1975 | Chatterjee | 128/290 R |
| 3,935,099 | 1/1976 | Weaver et al. | 210/43 |
| 3,936,441 | 2/1976 | Holst et al. . | |
| 3,965,091 | 6/1976 | Holst et al. . | |
| 3,971,379 | 7/1976 | Chatterjee | 128/285 |
| 3,981,100 | 9/1976 | Weaver et al. | 47/58 |
| 4,041,121 | 8/1977 | Smith | 264/191 |
| 4,043,952 | 8/1977 | Ganslaw et al. . | |
| 4,044,766 | 8/1977 | Kaczmarzyk et al. | 128/285 |
| 4,066,828 | 1/1978 | Holst et al. | 536/87 |
| 4,068,067 | 1/1978 | Holst et al. | 536/87 |
| 4,090,013 | 5/1978 | Ganslaw et al. | 526/15 |
| 4,117,222 | 9/1978 | Holst et al. | 536/50 |
| 4,127,944 | 12/1978 | Giacobello | 34/9 |

(List continued on next page.)

FOREIGN PATENT DOCUMENTS

| | | |
|---|---|---|
| 3574789 | 11/1989 | Australia . |
| 731146 | 3/1966 | Canada . |
| 2072918 | 8/1993 | Canada . |
| 0319865A2 | 6/1989 | European Pat. Off. . |
| 0509708A1 | 10/1992 | European Pat. Off. . |
| 0538904 | 4/1993 | European Pat. Off. . |
| 0566118 | 10/1993 | European Pat. Off. . |
| 56-084701A | 7/1981 | Japan . |
| 60-177001 | 9/1985 | Japan . |
| 2227435 | 12/1989 | Japan . |
| 4-120142A | 4/1992 | Japan . |
| 1086323 | 10/1967 | United Kingdom . |
| 1550614 | 8/1979 | United Kingdom . |
| 2104932B | 3/1983 | United Kingdom . |
| WO91/02552 | 3/1991 | WIPO . |

OTHER PUBLICATIONS

Formation of Amide Bonds in Chitosan Carboxymethyl Ether by M. R. Bazt, G. A. Vikhoreva, and L. S. Gal'braikh–translated from Khimicheskie Volokna, No. 5, pp. 5–6, Sep.–Oct. 1990 Plenum Publishing Corporation–pp. 294–296.

Absorbent Polymer Technology, edited by Lisa Brannon--Peppas and Ronald S. Harland–Studies in Polymer Science 8–Elsevier, Sep. 1990, Amsterdam.

Ionotropic Crosslinking of Sodium Carboxymethylcellulose and Sodium Carboxymethylcellulose–Gelatin Matrices and Their Erosion Properties–M. P. Prasad and M. Kalyanasundaram–Journal of Applied Polymer Science, vol. 49, No. 12, pp. 2075–2079 (Sep. 1993)–John Wiley & Sons.

*Primary Examiner*—Jeffrey Mullis, Ph.D.
*Attorney, Agent, or Firm*—Thomas J. Mielke; John R. Schenian

[57] ABSTRACT

Disclosed is a method for producing a water-swellable, generally water-insoluble modified polysaccharide having improved age-stable absorption properties. The method involves forming a mixture of a modified polysaccharide, water, and, optionally, a crosslinking agent, recovering the modified polysaccharide from the mixture and, optionally, heat-treating said recovered modified polysaccharide.

68 Claims, 1 Drawing Sheet

U.S. PATENT DOCUMENTS

| | | | |
|---|---|---|---|
| 4,155,888 | 5/1979 | Mooth. | |
| 4,169,121 | 9/1979 | Pietsch et al. | 264/103 |
| 4,195,175 | 3/1980 | Peniston et al. | 536/20 |
| 4,200,736 | 4/1980 | Shinohara et al. | 536/87 |
| 4,252,761 | 2/1981 | Schoggen et al. | 264/120 |
| 4,256,877 | 3/1981 | Karlson et al. | 536/59 |
| 4,340,731 | 7/1982 | Colombo et al. | 536/87 |
| 4,373,096 | 2/1983 | Koshugi | 536/20 |
| 4,404,371 | 9/1983 | Bellmann et al. | 536/98 |
| 4,410,694 | 10/1983 | Nakayama et al. | 536/98 |
| 4,454,055 | 6/1984 | Richman et al. | 252/194 |
| 4,483,950 | 11/1984 | Fanta et al. | 524/48 |
| 4,493,928 | 1/1985 | Koshugi | 536/20 |
| 4,521,594 | 6/1985 | Kanematu | 536/98 |
| 4,650,716 | 3/1987 | Gelman | 428/402 |
| 4,683,298 | 7/1987 | Yalpani | 536/45 |
| 4,689,408 | 8/1987 | Gelman et al. | 536/98 |
| 4,697,008 | 9/1987 | Asano et al. | 536/89 |
| 4,734,478 | 3/1988 | Tsubakimoto et al. | 527/300 |
| 4,758,617 | 7/1988 | Tanioku et al. | 524/413 |
| 4,820,307 | 4/1989 | Welch et al. | 8/120 |
| 4,952,550 | 8/1990 | Wallach et al. | 502/404 |
| 4,990,551 | 2/1991 | Haubl et al. | 524/30 |
| 5,001,232 | 3/1991 | Herzog et al. | 536/90 |
| 5,005,771 | 4/1991 | Pieh et al. | 241/23 |
| 5,079,354 | 1/1992 | Gross et al. | 536/111 |
| 5,126,382 | 6/1992 | Hollenberg | 524/56 |
| 5,137,537 | 8/1992 | Herron et al. | 8/120 |
| 5,147,343 | 9/1992 | Kellenberger | 604/368 |
| 5,149,335 | 9/1992 | Kellenberger et al. | 604/372 |
| 5,247,072 | 9/1993 | Ning et al. | 536/97 |

MODIFIED POLYSACCHARIDES HAVING IMPROVED ABSORBENT PROPERTIES AND PROCESS FOR THE PREPARATION THEREOF

This application is a continuation-in-part of U.S. patent application Ser. No. 07/870,529, filed Apr. 17, 1992, now abandoned.

BACKGROUND OF THE INVENTION

1. Field of the Invention

The present invention relates to modified polysaccharides having improved absorbent properties. Specifically, the present invention relates to modified polysaccharides having an improved ability to absorb liquid while under an external pressure and after aging and a process for the preparation thereof.

2. Description of the Related Art

The use of water-swellable, generally water-insoluble, absorbent materials, commonly known as superabsorbents, in disposable absorbent personal care products is known. Such absorbent materials are generally employed in absorbent products such as diapers, training pants, adult incontinence products, and feminine care products in order to increase the absorbent capacity of such products while reducing their overall bulk. Such absorbent materials are generally present in absorbent products in a fibrous matrix, such as a matrix of wood pulp fluff. A matrix of wood pulp fluff generally has an absorbent capacity of about 6 grams of liquid per gram of fluff. The absorbent materials described above generally have an absorbent capacity of at least about 10, preferably of about 20, and often of up to 100 times their weight in water. Clearly, incorporation of such absorbent materials in personal care products can reduce the overall bulk while increasing the absorbent capacity of such products.

A wide variety of materials have been described for use as absorbent materials in such personal care products. Such materials include natural-based materials such as agar, pectin, gums, carboxyalkyl starch, and carboxyalkyl cellulose, as well as synthetic materials such as polyacrylates, polyacrylamides, and hydrolyzed polyacrylonitrile. While the natural-based, absorbent materials are known for use in personal care products, they have not gained wide usage in such products. The natural-based, absorbent materials have not gained wide usage in personal care products, at least in part, because their absorbent properties are generally inferior compared to the synthetic absorbent materials, such as the polyacrylates. Specifically, many of the natural-based materials tend to form soft, gelatinous masses when swollen with a liquid. When employed in absorbent products, the presence of such soft gelatinous masses tends to prevent the transport of liquid within the fibrous matrix in which the absorbent materials are incorporated. This phenomenon is known as gel-blocking. Once gel-blocking occurs, subsequent insults of liquid cannot be efficiently absorbed by the product, and the product tends to leak. Further, many of the natural-based materials exhibit poor absorption properties, particularly when subjected to external pressures.

In contrast, the synthetic, absorbent materials are often capable of absorbing large quantities of liquid while maintaining a generally stiff, non-mucilaginous character. Accordingly, the synthetic, absorbent materials can be incorporated in absorbent products while minimizing the likelihood of gel-blocking.

Carboxyalkyl cellulose materials and other modified polysaccharides are known in the art. As a general rule, carboxyalkyl cellulose materials are formed from a cellulosic material which has been treated with carboxyalkylating reactants, such as a chloroalkanoic acid, preferably monochloroacetic acid, and an alkali, such as sodium hydroxide, optionally, in the presence of an alcohol. Such a process is described, for example, in U.S. Pat. No. 3,723,413, issued Mar. 27, 1973, to Chatterjee et al. Such carboxyalkyl celluloses are generally water soluble. Various methods of rendering such water-soluble carboxyalkyl celluloses water insoluble are known.

U.S. Pat. No. 2,639,239 issued May 19, 1953, to Elliott describes a process in which a commercially available water-soluble, alkali-metal salt of carboxymethyl cellulose, having a degree of substitution of from about 0.5 to about 1, is subjected to a thermal treatment for up to 10 hours which renders such water-soluble carboxymethyl cellulose capable of forming highly-swollen gel particles.

Similarly, U.S. Pat. No. 3,723,413, discussed above, describes the heat-treatment of a carboxyalkyl cellulose in the presence of remaining carboxyalkylating reactants and by-products, such that, the carboxyalkyl cellulose becomes water insoluble and possessed of desirable liquid absorptive and retentive properties and characteristics.

U.S. Pat. No. 3,345,358 issued Oct. 3, 1967, to Inklaar describes a method of preparing a gel-forming derivative of polysaccharides such as carboxymethyl starch. The method involves acidifying finely divided carboxymethyl ethers of polysaccharides by treating them with acid in methanol or other water-miscible, organic liquid medium. In this manner, acid carboxymethyl groups are formed on the material. The material is held under acidified, non-hydrolyzing conditions to bring about the formation of ester bonds whereby constituent macromolecules of the material become crosslinked one to another. The material is then neutralized with an alkali. The derivatives so produced are described as being capable of forming a gel upon addition to water.

U.S. Pat. No. 3,379,720 issued Apr. 23, 1968, to Reid describes a process of preparing modified polysaccharides, such as ethers and esters of cellulose, comprising slurrying a water-soluble polysaccharide in any inert medium, acidifying said polysaccharide, removing excess acid from the acidified polysaccharide, drying same and heat-curing.

U.S. Pat. No. 4,689,408 issued Aug. 25, 1987, to Gelman et al. describes a method of preparing salts of carboxymethyl cellulose. The method involves treating a carboxymethyl cellulose with water, adding a nonsolvent for the carboxymethyl cellulose, and recovering the carboxymethyl cellulose. The carboxymethyl cellulose is said to have an absorbency of at least 25 grams of liquid per gram of carboxymethyl cellulose.

Unfortunately, the known modified polysaccharide materials do not possess absorptive properties comparable to many of the synthetic, highly-absorptive materials. This has prevented widespread use of such carboxyalkyl polysaccharides in absorbent personal care products.

It is desirable to develop and produce a natural-based, highly absorbent material having age-stable absorptive properties similar to the synthetic, highly absorptive materials and, thus, suitable for use in personal care absorbent products.

SUMMARY OF THE INVENTION

The present invention concerns a water-swellable, water-insoluble carboxyalkyl polysaccharide. The carboxyalkyl polysaccharide is characterized in that it exhibits an effective initial Absorbency Under Load (AUL) value and exhibits an effective stability in its absorbent properties after aging.

One embodiment of the present invention concerns a carboxyalkyl polysaccharide that exhibits an initial Absorbency Under Load value of at least about 14 and retains at least about 50 percent of its initial Absorbency Under Load value after aging for about 60 days at about 24° C. and at least about 30 percent relative humidity.

The present invention further concerns methods for producing a water-swellable, water-insoluble carboxyalkyl polysaccharide that exhibits an effective initial Absorbency Under Load value and exhibits an effective stability in its absorbent properties after aging.

One method of the present invention comprises the steps of preparing a mixture comprising a water-soluble carboxyalkyl polysaccharide, water, and a crosslinking agent. The carboxyalkyl polysaccharide is recovered from the mixture and heat-treated at a temperature for an amount of time effective so that the carboxyalkyl polysaccharide exhibits an effective initial Absorbency Under Load value and exhibits an effective stability in its absorbent properties after aging.

One embodiment of such a method comprises forming a mixture comprising a water-soluble carboxyalkyl polysaccharide, water, and a crosslinking agent; recovering said carboxyalkyl polysaccharide from said mixture; and heat-treating said recovered carboxyalkyl polysaccharide at a temperature above about 50° C. for a time effective to crosslink said carboxyalkyl polysaccharide to render said carboxyalkyl polysaccharide water swellable and water insoluble, wherein the water-swellable, water-insoluble carboxyalkyl polysaccharide exhibits an initial Absorbency Under Load value of at least about 14 and retains at least about 50 percent of the initial Absorbency Under Load value after aging for about 60 days at about 24° C. and at least about 30 percent relative humidity.

Another method of the present invention comprises the steps of preparing a mixture comprising a water-soluble carboxyalkyl polysaccharide and water. The carboxyalkyl polysaccharide is recovered from the mixture and heat-treated at a temperature for an amount of time effective so that the carboxyalkyl polysaccharide exhibits an effective initial Absorbency Under Load value and exhibits an effective stability in its absorbent properties after aging.

One embodiment of such a method comprises forming a mixture comprising a water-soluble carboxyalkyl polysaccharide, and water; recovering said carboxyalkyl polysaccharide from said mixture; and heat-treating said recovered carboxyalkyl polysaccharide at a temperature between about 200° C. and about 250° C. for an amount of time between about 50 to about 90 seconds, wherein said heat-treating is effective to crosslink said carboxyalkyl polysaccharide to render said carboxyalkyl polysaccharide water swellable and water insoluble, wherein the water-swellable, water-insoluble carboxyalkyl polysaccharide exhibits an initial Absorbency Under Load value of at least about 14 and retains at least about 50 percent of the initial Absorbency Under Load value after aging for about 60 days at about 24° C. and at least about 30 percent relative humidity.

Another method of the present invention comprises the steps of preparing a mixture comprising a water-soluble carboxyalkyl polysaccharide and water, wherein the mixture has a pH between about 4.0 and about 7.5. The carboxyalkyl polysaccharide is recovered from the mixture and heat-treated at a temperature for an amount of time effective so that the carboxyalkyl polysaccharide exhibits an effective initial Absorbency Under Load value and exhibits an effective stability in its absorbent properties after aging.

One embodiment of such a method comprises forming a mixture comprising a water-soluble carboxyalkyl polysaccharide and water, wherein the mixture has a pH between about 4.0 and about 7.5; recovering said carboxyalkyl polysaccharide from said mixture; and heat-treating said recovered carboxyalkyl polysaccharide at a temperature above about 50° C. for a time effective to crosslink said carboxyalkyl polysaccharide to render said carboxyalkyl polysaccharide water swellable and water insoluble, wherein the water-swellable, water-insoluble carboxyalkyl polysaccharide exhibits an initial Absorbency Under Load value of at least about 14 and retains at least about 50 percent of the initial Absorbency Under Load value after aging for about 60 days at about 24° C. and at least about 30 percent relative humidity.

Another method of the present invention comprises the steps of preparing a mixture comprising a water-soluble carboxyalkyl polysaccharide, citric acid, a catalyst, and water. The carboxyalkyl polysaccharide is recovered from the mixture so that the carboxyalkyl polysaccharide exhibits an effective initial Absorbency Under Load and exhibits an effective stability in its absorbent properties after aging.

One embodiment of such a method comprises forming a mixture comprising a water-soluble carboxyalkyl polysaccharide, water, citric acid, and sodium hypophosphite and recovering said carboxyalkyl polysaccharide from said mixture, wherein the water-swellable, water-insoluble carboxyalkyl polysaccharide exhibits an initial Absorbency Under Load value of at least about 14 and retains at least about 50 percent of the initial Absorbency Under Load value after aging for about 60 days at about 24° C. and at least about 30 percent relative humidity.

Another method of the present invention comprises the steps of forming a mixture comprising a water-soluble carboxyalkyl polysaccharide, an aluminum ion, and water. The carboxyalkyl polysaccharide is recovered from the mixture so that the carboxyalkyl polysaccharide exhibits an effective initial Absorbency Under Load and exhibits an effective stability in its absorbent properties after aging.

One embodiment of such a method comprises forming a mixture comprising a water-soluble carboxyalkyl polysaccharide, water, and a crosslinking agent comprising an aluminum ion and recovering said carboxyalkyl polysaccharide from said mixture wherein the water-swellable, water-insoluble carboxyalkyl polysaccharide exhibits an initial Absorbency Under Load value of at least about 14 and retains at least about 50 percent of the initial Absorbency Under Load value after aging for about 60 days at about 24° C. and at least about 30 percent relative humidity.

Another method of the present invention comprises preparing a carboxyalkyl polysaccharide in a reaction dispersion, recovering the carboxyalkyl polysaccharide from the reaction dispersion, preparing a mixture comprising the recovered carboxyalkyl polysaccharide and water, and recovering the carboxyalkyl polysaccharide from the mixture wherein the carboxyalkyl polysaccharide comprises an amount of the original crystalline structure of the polysaccharide to be effective so that the carboxyalkyl polysaccharide exhibits an effective initial Absorbency Under Load and exhibits an effective stability in its absorbent properties after aging.

One embodiment of such a method comprises:
a. preparing a reaction dispersion comprising a solvent and a polysaccharide comprising an original crystalline structure;

b. adding a carboxyalkylating reagent to the reaction dispersion at conditions effective to allow the carboxyalkylating reagent to react with the polysaccharide to prepare a carboxyalkyl polysaccharide;

c. recovering the carboxyalkyl polysaccharide from the reaction dispersion;

d. preparing a mixture comprising the recovered carboxyalkyl polysaccharide and water; and e. recovering the carboxyalkyl polysaccharide from the mixture wherein the carboxyalkyl polysaccharide comprises an amount of the original crystalline structure of the polysaccharide to be effective to result in the water-swellable, water-insoluble carboxyalkyl polysaccharide exhibiting an initial Absorbency Under Load value of at least about 14 and retaining at least about 50 percent of the initial Absorbency Under Load value after aging for about 60 days at about 24° C. and at least about 30 percent relative humidity.

DETAILED DESCRIPTION OF THE PREFERRED EMBODIMENTS

Figure 1:
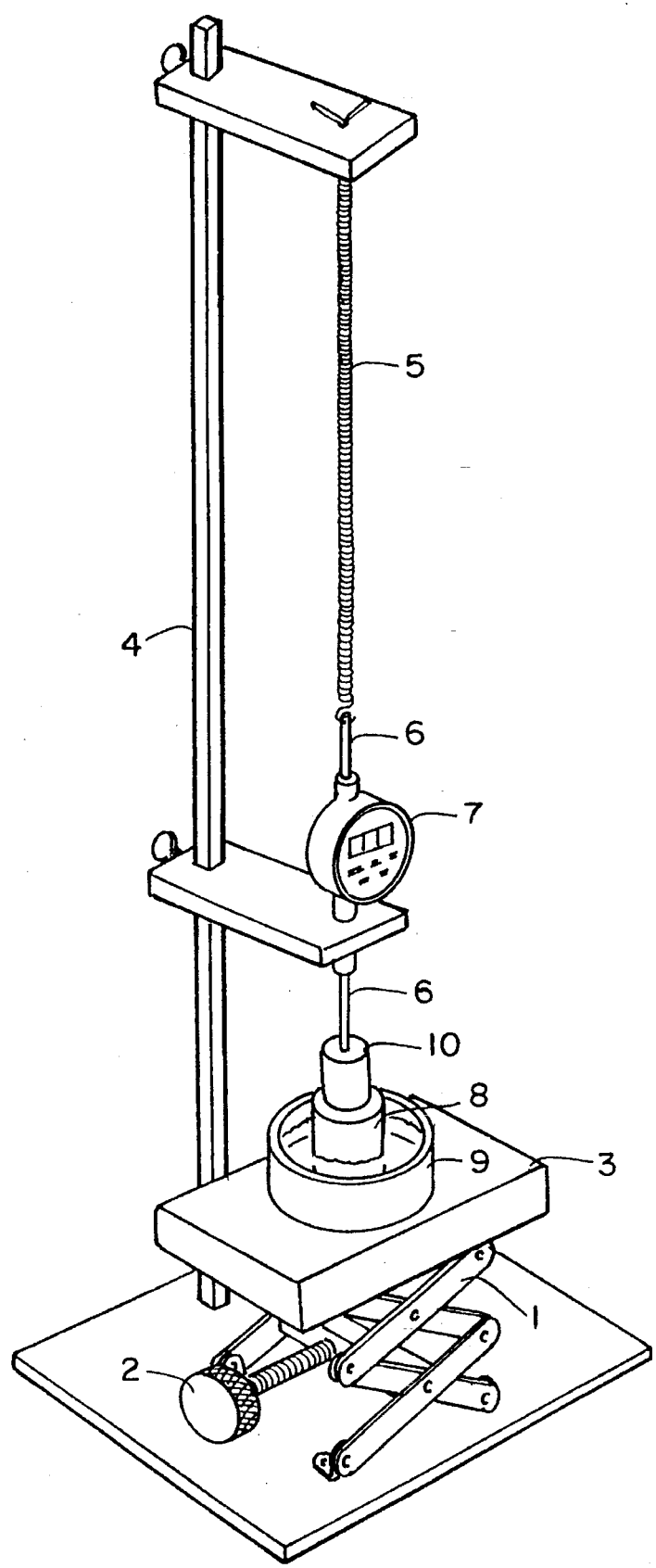
FIG. 1 illustrates the apparatus for determining the Absorbency Under Load values of an absorbent material.

In one aspect, the present invention concerns a water-swellable, water-insoluble modified polysaccharide that initially exhibits effective absorbency properties and substantially retains such absorbency properties after aging.

Modified polysaccharides suitable for use in the present invention are generally water soluble prior to treatment of the modified polysaccharide to provide the modified polysaccharide with the desired initial and age-stable absorbency characteristics as disclosed herein. As used herein, a modified polysaccharide will be considered to be water soluble when it substantially dissolves in excess water to form a true solution, thereby losing its initially particulate form and becoming molecularly dispersed throughout the water solution. Alternatively, the modified polysaccharide may swell in water to such an extent that it appears to lose its initial structure even though a true solution may not be formed. As a general rule, the water-soluble modified polysaccharides will be free from a substantial degree of crosslinking, as crosslinking tends to render the modified polysaccharides water insoluble.

As used herein, the term "water-swellable, water-insoluble" is meant to refer to a modified polysaccharide that, when exposed to an excess of a 0.9 weight percent solution of sodium chloride in water, swells to its equilibrium volume but does not dissolve into the solution. As such, a water-swellable, water-insoluble modified polysaccharide generally retains its original identity or physical structure, but in a highly expanded state, during the absorption of the aqueous solution and, thus, must have sufficient physical integrity to resist flow and fusion with neighboring particles. A water-swellable, water-insoluble modified polysaccharide useful in the present invention is one which is effectively crosslinked to be substantially insoluble but still is initially capable of absorbing at least about 14 times its own weight of a 0.9 weight percent solution of sodium chloride in water when under an applied load of about 0.3 pound per square inch.

Modified polysaccharides suitable for use in the present invention include, without limitation, the carboxylated, sulfonated, sulfated, and phosphated derivatives of polysaccharides, their salts, and mixtures thereof. Exemplary of suitable polysaccharides are cellulose, starch, guar, carrageenan, agar, gellan gum, chitin, chitosan and mixtures thereof.

Suitable carboxyalkyl polysaccharides for use in the present invention include carboxyalkyl celluloses such as carboxymethyl cellulose, carboxyethyl cellulose, carboxyalkyl starch, carboxyalkyl carrageenan, carboxyalkyl agar, carboxyalkyl gellan gum, and mixtures thereof. A beneficial carboxyalkyl polysaccharide is a carboxyalkyl cellulose with a beneficial carboxyalkyl cellulose being carboxymethyl cellulose.

Methods of making carboxyalkyl polysaccharides are known to those skilled in the art. Suitably, a polysaccharide material such as wood pulp fluff, cotton, cotton linters, starch, and agar are provided. The polysaccharide material may be in the form of fibers or of fibers which have been comminuted to particulate form. Typically, the polysaccharide material is dispersed in a solvent, such as water or an alcohol, and carboxyalkylating reagents added to the dispersion. Carboxyalkylating reagents generally comprise a chloroalkanoic acid, such as monochloroacetic acid, and a base, such as sodium hydroxide. The carboxyalkylating reagents are added to the dispersion at conditions effective to allow the carboxyalkylating reagents to react with and modify the polysaccharide. Such effective conditions can vary and will typically depend on, for example, temperature, pressure, mixing conditions, and relative amounts of materials, solvents and reagents used in the modification of the polysaccharide.

One process of the present invention comprises preparing the carboxyalkyl polysaccharide from a polysaccharide comprising an original crystalline structure and retaining an effective amount of the original polysaccharide crystallinity wherein such retained crystallinity functions as a crosslinking moiety so that the carboxyalkyl polysaccharide exhibits an effective initial Absorbency Under Load value and exhibits an effective stability in its absorption properties after aging.

In such a process, the polysaccharide material is dispersed in a solvent and carboxyalkylating reagents are added to the dispersion. The carboxyalkylating reagents are added to the dispersion at conditions effective to allow the carboxyalkylating reagents to react with and modify the polysaccharide while retaining an effective amount of the original crystallinity of the polysaccharide. Such effective conditions can vary and will typically depend on, for example, temperature, pressure, mixing conditions, and types and relative amounts of materials, solvents and reagents used. The carboxyalkyl polysaccharide is then generally recovered from the dispersion. The recovered carboxyalkyl polysaccharide is then dispersed in an aqueous mixture and recovered from the mixture as, for example, using the methods described herein. Such a final-recovered crystalline-crosslinked carboxyalkyl polysaccharide comprises an amount of the original crystalline structure of the polysaccharide to be effective to result in the crystalline-crosslinked carboxyalkyl polysaccharide exhibiting an effective initial Absorbency Under Load value and exhibiting an effective stability after aging.

Many polysaccharides, such as cellulose and chitin, are known to be highly crystalline materials. The degree of crystallinity depends on the source of the polysaccharide and its processing history. The highly-ordered crystalline structures and the less-ordered amorphous areas generally have different reactivities toward incoming chemicals. The result of this difference in reactivities is that the amorphous areas are generally substituted first and heaviest, whereas the highly crystalline areas are substituted last and least. Alkali swelling of the polysaccharide improves the accessibility of the modifying reagents into the crystalline areas and facilitates the modifying reactions. If the overall degree of substitution of the polysaccharide is sufficiently high and the modification relatively uniformly distributed, total solubility of the modified polysaccharide in an aqueous solution is generally achieved. However, if the overall degree of substitution is relatively low, or the modification relatively unevenly distributed, the resulting modified polysaccharide will have a chain structure of alternating soluble and insoluble segments like a block copolymer. The insoluble segments would generally be in the crystalline areas remaining after the modification reaction. Such a crystalline area functions as a crosslinking point for the soluble modified polysaccharide segments. Such crystallinity of the initial polysaccharide or of the modified final product may be determined by analytical methods such as optical microscopy and x-ray diffraction. The modified final product, after dispersion in an aqueous solution, may retain some of the fibrous characteristics of the initial polysaccharide.

Using carboxymethylation of cellulose as an example for discussion purposes, carboxymethylation is a modification process which is generally considered kinetically controlled and irreversible. Once the carboxymethyl substitution has taken place, the arrangement of the carboxymethyl groups along the cellulose chain is generally fixed. The particular pattern of carboxymethyl substitution on cellulose obtained depends on the reactant ratios and reaction conditions during the synthesis.

In cellulose, the more accessible amorphous regions tend to be substituted preferentially over the crystalline regions. Consequently, the carboxymethyl groups are not uniformly distributed along the cellulose chain. Using excess alkali, or pushing the reaction to a higher degree of substitution, allows substitution to occur in the crystalline regions, leading to more uniform patterns of substitution and more complete water solubility.

Conversely, the survival of the native cellulose crystalline areas could be encouraged by certain conditions. For example, a crystalline-crosslinked carboxymethyl cellulose has been found to be capable of being prepared by different processes including: using potassium hydroxide as compared to sodium hydroxide as the alkali in the process; using a less than stoichiometric ratio of alkali to carboxyalkylating reagent, such as chloroacetic acid; using a lower reactant ratio of carboxymethylating reagents to cellulose; varying the solvent composition in the slurry process; or a combination of these different process techniques. Such reaction conditions can be designed to promote carboxymethyl cellulose structures which have crystalline cellulose segments as well as carboxyalkylated segments in the final molecular structures. One typical result of this molecular structure is that, when the aforementioned carboxymethyl cellulose is dissolved in water, the dispersion remains translucent or fibrous; whereas a soluble, relatively uniformly substituted carboxymethyl cellulose results in a solution that is clear and transparent.

Alkali is used in the preparation of carboxymethyl cellulose as both a swelling agent for the cellulose and a neutralizing chemical for any acids, such as hydrochloric acid, released by the carboxymethylation reaction. Sodium hydroxide is generally used as the alkali in commercial carboxymethyl cellulose manufacturing processes. It has been found that the use of potassium hydroxide as the alkali in the carboxymethylation of cellulose tends to produce a more unevenly distributed carboxymethylation pattern, even at a relatively high degree of substitution, than the use of sodium hydroxide. Such an unevenly distributed carboxymethylation pattern generally helps preserve part of the native crystallites in the final carboxymethyl polysaccharide product which generally results in improved absorbent properties of the carboxymethyl polysaccharide. Conversely, the same process, but with sodium hydroxide in place of potassium hydroxide as the alkali, results in a water-soluble carboxymethyl cellulose with relatively poorer absorbent properties.

The differences between using potassium hydroxide as compared to using sodium hydroxide is believed to be related to the solvation power of the potassium ion. Being a larger cation than the sodium ion, the potassium ion may not be able to penetrate some of the cellulose crystalline regions, leaving such cellulose crystalline regions generally intact during carboxymethylation and, thus, resulting in a more unevenly distributed substitution pattern. Such an unevenly distributed substitution pattern can happen even with relatively highly-substituted carboxymethyl cellulose as, for example, with a degree of substitution greater than 1.

Use of an excess amount of alkali relative to the carboxyalkylating reagent, such as chloroacetic acid, generally produces a more evenly substituted carboxymethyl cellulose product which is water soluble when the degree of substitution is sufficiently high. However, it has been found that, where there is a deficiency of alkali relative to the carboxyalkylating agent, a water-insoluble and relatively unevenly substituted carboxymethyl cellulose with desirable absorbent properties may be produced. This phenomenon is believed to occur because a deficiency in alkali relative to the carboxyalkylating reagent reduces the degree of swelling in the cellulose structure which, in turn, promotes preferential substitution in the amorphous regions as compared to the crystalline regions.

Use of a relatively low ratio of carboxyalkylating reagent to polysaccharide, such as of chloroacetic acid to cellulose, may also be used to produce a carboxyalkyl polysaccharide with desirable absorbent properties. In addition, the use of a relatively low ratio of carboxyalkylating reagent to polysaccharide generally means lower raw material costs and less reaction by-products, both of which are generally beneficial for economic and environmental reasons.

Such crystalline-crosslinked carboxyalkyl polysaccharides generally need to be treated with a homogenization process, such as by dispersion and recovery from an aqueous mixture, but generally do not need any additional processing steps, such as heat or chemical treatment, in order to exhibit the desired initial AUL value and age-stable absorbency properties described in this invention.

Through dispersion of the crystalline-crosslinked carboxyalkyl cellulose in water, the fibrous structure and the molecular alignment of the modified cellulose chains are reduced. As the soluble segments of the carboxyalkyl cellulose chains start to interpenetrate one another in the dispersion, a random, coil-entangled molecular configuration is created which is subsequently locked in upon drying. Larger aggregates of the crystalline areas might also be formed in the dissolution process which serve as super-junction zones for the carboxyalkyl cellulose chains, allowing a truly three-dimensional network to evolve.

Repeated liquid uptake and removal do not seem to affect the absorbent properties of the crystalline-crosslinked carboxyalkyl cellulose. The stability of the physical crosslinks is believed to be dependent on the size of the crystalline areas that serve as the crosslinking junctions. Once the crystalline areas are above an effective range, as for example above the micron range, the junctions are stable and will generally not be susceptible to the attack of water molecules. Such an effective size of the crystalline areas is generally reflected in the translucency of the dispersion of the crystalline-crosslinked carboxymethyl cellulose in an aqueous solution. Any method of recovering the carboxyalkyl polysaccharide from a reaction dispersion, without unacceptably deteriorating the absorption characteristics of the carboxyalkyl polysaccharide, is suitable for use in the present invention. Examples of such methods include evaporative drying, freeze drying, precipitation, critical point drying, and the like. However, it is to be understood that it may be possible to perform the carboxyalkylation of the starting polysaccharide in such a manner that a solution of carboxyalkyl polysaccharide and water can be formed directly, without the need of an intermediate recovery step. For example, the modification process may be performed under low moisture conditions. That is, the starting polysaccharide may be wetted with, for example, 1 part of water for each part of starting polysaccharide. Carboxyalkylating reagents can then be mixed with the wetted starting polysaccharide such that carboxyalkylation occurs. Additional water can then be added to the carboxyalkyl polysaccharide to form a mixture of carboxyalkyl polysaccharide and water. In this manner, no recovery step may be necessary between formation of the carboxyalkyl polysaccharide and any further treatment steps, such as the preparation of a mixture of carboxyalkyl polysaccharide and water, in order to impart the aging stability to the carboxyalkyl polysaccharide. If too much water is present in the starting polysaccharide, however, the carboxyalkylation reaction may not occur to a sufficient degree.

When the carboxyalkyl polysaccharide is a carboxyalkyl cellulose, the carboxyalkyl celluloses suitable for use in the present invention generally have an average degree of substitution from about 0.3 to about 1.5, suitably from about 0.4 to about 1.2. The degree of substitution refers to the average number of carboxylalkyl groups, such as carboxymethyl groups, present on the anhydroglucose unit of the cellulosic material. Generally, the maximum average number of carboxylalkyl groups that may be present on the anhydroglucose unit of the cellulosic material is 3.0. When the carboxyalkyl celluloses have an average degree of substitution within the range of from about 0.3 to about 1.5, the carboxyalkyl celluloses are generally water soluble prior to treatment of the carboxyalkyl celluloses to provide the carboxyalkyl celluloses with the desired initial and age-stable absorbency properties of the present invention. However, one skilled in the art will appreciate that other characteristics, such as the actual pattern of modifying substitution of the polysaccharide, may also have an effect on the water-solubility of the carboxyalkyl polysaccharide.

Carboxyalkyl cellulose is available in a wide range of molecular weights. Carboxyalkyl cellulose having a relatively high molecular weight is often beneficial for use in the present invention. Nonetheless, a wide range of molecular weights are suitable for use in the present invention. It is generally most convenient to express the molecular weight of a carboxyalkyl cellulose in terms of its viscosity in a 1.0 weight percent aqueous solution at 25° C. Carboxymethyl celluloses suitable for use in the present invention will generally have a viscosity in a 1.0 weight percent aqueous solution at 25° C. of from about 10 centipoise (10 mPa.s) to about 80,000 centipoise (80,000 mPa.s), beneficially from about 500 centipoise (500 mPa.s) to about 80,000 centipoise (80,000 mPa.s), and more beneficially from about 1,000 centipoise (1,000 mPa.s) to about 80,000 centipoise (80,000 mPa.s).

The crosslinked carboxyalkyl polysaccharides exhibiting improved absorbent properties of the present invention have been found to exhibit relatively low aqueous solution viscosities as compared to carboxyalkyl polysaccharides that do not exhibit the improved absorbent properties of the present invention. For example, when measured as a 1.0 weight percent amount in a 0.9 weight percent sodium chloride (saline) aqueous solution that has been allowed to reach equilibrium at about 25° C. as, for example, after about 18 hours of mixing, the carboxyalkyl polysaccharides of the present invention have been found to exhibit a viscosity of less than about 400 centipoise, beneficially less than about 300 centipoise, and suitably less than about 200 centipoise. The carboxyalkyl polysaccharides of the present invention have been found to exhibit viscosities that are typically about 50 percent, beneficially about 60, and suitably about 70 percent less than the viscosity exhibited by an otherwise identical carboxyalkyl polysaccharide that has not been prepared or treated to exhibit the improved absorbent properties of the present invention. For example, if a carboxyalkyl polysaccharide that has not been prepared or treated to exhibit the improved absorbent properties of the present invention exhibits a viscosity of about 800 centipoise, a carboxyalkyl polysaccharide that has been prepared or treated to exhibit the improved absorbent properties of the present invention will typically exhibit a viscosity of less than about 400 centipoise, beneficially less than about 320 centipoise, and suitably less than about 240 centipoise.

The method according to the present invention is found to produce an improvement in initial AUL values in modified polysaccharides over a wide range of molecular weights. While high molecular weight, modified polysaccharides are generally preferred, it is important that improvements in low molecular weight, modified polysaccharides can be achieved. Low molecular weight, modified polysaccharides are generally cheaper than high molecular weight, modified polysaccharides. Accordingly, there is an economic advantage for employing low molecular weight, modified polysaccharides. Further, it is possible to work with aqueous solutions containing relatively high concentrations of low molecular weight, modified polysaccharides compared to aqueous solutions containing high concentrations of high molecular weight, modified polysaccharides. This is because aqueous solutions of high molecular weight, modified polysaccharides exhibit a high viscosity compared to an aqueous solution containing the same concentration of low molecular weight, modified polysaccharides. Again, for reasons of efficiency, it is often desirable to form an aqueous solution comprising the highest concentration of modified polysaccharides possible while still being able to effectively work with the aqueous solution.

Suitable carboxyalkyl celluloses are commercially available from numerous vendors. Exemplary of a commercially available carboxyalkyl cellulose is carboxymethyl cellulose, commercially available from the Aqualon Company under the trade designation AQUALON® or BLANOSE® Cellulose Gum.

The carboxyalkyl polysaccharides of the present invention have the ability to absorb a liquid while the carboxyalkyl polysaccharide is under an external pressure or load, herein referred to as Absorbency Under Load (AUL). Synthetic polymeric materials, such as polyacrylates, having a generally high ability to absorb while under a load, have been found to minimize the occurrence of gel-blocking when incorporated in absorbent products. The method by which the Absorbency Under Load is determined is set forth below in connection with the examples. The Absorbency Under Load values determined as set forth below and reported herein refer to the amount, in grams, of an aqueous solution containing 0.9 weight percent sodium chloride a gram of the modified polysaccharide can absorb in 60 minutes under a load, for example, of about 0.3 pound per square inch (psi). As a general rule, it is desired that the carboxyalkyl polysaccharide has an initial Absorbency Under Load value, for a load of about 0.3 psi, of at least about 14, beneficially of at least about 17, more beneficially of at least about 20, suitably of at least about 24, more suitably of at least about 27, and up to about 50 grams per gram. As used herein, the term "initial Absorbency Under Load" is meant to refer to that AUL value exhibited by a carboxyalkyl polysaccharide as measured within 1 day after preparation of the carboxyalkyl polysaccharide when the carboxyalkyl polysaccharide is stored at ambient conditions, such as at about 24° C. and between about 30 to about 60 percent relative humidity. The conditions under which a carboxyalkyl polysaccharide is stored have been found to potentially have an impact on the absorbent properties of the carboxyalkyl polysaccharide as it ages. Even relatively mild conditions, such as ambient conditions, such as about 24° C. and at least about 30 percent relative humidity, suitably between about 30 to about 60 percent relative humidity, will typically result in a degradation of the absorbent properties of the carboxyalkyl polysaccharide as it ages. Typically, storage conditions, such as relatively higher temperatures and/or relatively higher relative humidities, as compared to ambient conditions, may result in quicker and/or more severe degradation of the absorbent properties of the carboxyalkyl polysaccharide as it ages.

Carboxyalkyl polysaccharides of the present invention will tend to retain their initial AUL value after aging. Specifically, carboxyalkyl polysaccharides of the present invention may retain greater than about 50 percent, and suitably greater than about 70 percent, of their initial AUL value after aging for about 60 days. Typically, the aging conditions are at ambient conditions, such as at about 24° C. and at least about 30 percent relative humidity. For example, if a carboxyalkyl polysaccharide of the present invention has an initial AUL value of about 20, that carboxyalkyl polysaccharide may have an AUL value of at least about 10, and suitably of about 14, after aging for about 60 days at about 24° C. and at least about 30 percent relative humidity. Otherwise similar carboxyalkyl polysaccharides tend not to retain their initial AUL value after aging under similar conditions.

Suitably, the carboxyalkyl polysaccharides of the present invention retain greater than about 50 percent, and more suitably greater than about 70 percent, of their initial AUL value after aging for about 60 days at about 24° C. and about 100 percent relative humidity.

As described above, the carboxyalkyl polysaccharide is suitably a carboxyalkyl cellulose, such as carboxymethyl cellulose or carboxyethyl cellulose. Such a carboxyalkyl cellulose suitably has an initial Absorbency Under Load value of at least about 14, beneficially of at least about 17, more beneficially of at least about 20, suitably of at least about 24, and more suitably of at least about 27 and retains greater than about 50 percent, and suitably greater than about 70 percent, of its initial AUL value after aging for about 60 days at about 24° C. and at least about 30 percent relative humidity and, suitably, retains greater than about 50 percent, beneficially greater than about 70 percent, of its initial AUL value after aging for about 60 days at about 24° C. and about 100 percent relative humidity.

Without intending to be bound thereby, it is hypothesized that the aging phenomenon in regards to the AUL is due to the disassociation of crosslinking points of the carboxyalkyl polysaccharide. Crosslinking points can generally be divided into two groups. First, crosslinking points can be of a relatively permanent crosslinking, such as with ester or amide linkages, resulting, for example, by the use of a polyamine crosslinking agent, or with ionic bonding, resulting, for example, by the use of a polyvalent metal ion crosslinking agent, or with physical crosslinks resulting, for example, from a retained crystalline structure. Second, crosslinking points can be of a relatively temporary crosslinking, such as with hydrogen bonding within the carboxyalkyl polysaccharide. In order to improve the aging stability of the carboxyalkyl polysaccharide, it is believed to be desirable to increase the amount of relatively permanent crosslinking that exists within the carboxyalkyl polysaccharide but not to such an extent as to over-crosslink the carboxyalkyl polysaccharide.

The carboxyalkyl polysaccharides of the present invention are suitable for use in disposable absorbent garments such as personal care products, such as diapers, training pants, feminine care products, adult incontinent products, and medical products such as wound dressings or surgical capes or drapes.

It has been found that the modified polysaccharides of the present invention may be prepared by a variety of processes. In general, an aqueous mixture of a water-soluble carboxyalkyl polysaccharide, water and, optionally, a crosslinking agent, is prepared. Such an aqueous mixture generally comprises from about 0.01 to about 90 weight percent, beneficially from about 0.1 to about 30 weight percent, and suitably from about 2 to about 25 weight percent, based on total mixture weight, of the carboxyalkyl polysaccharide. The mixture generally comprises from about 99.99 to about 10 weight percent, beneficially from about 99.9 to about 70 weight percent, and suitably from about 98 to about 75 weight percent water.

The dissolution of the carboxyalkyl polysaccharide into an aqueous mixture is believed to result in entanglement of individual segments of the carboxyalkyl polysaccharide with each other. Such entanglement results in the polysaccharide chains interpenetrating one another in the mixture, so that a random, coil-entangled molecular configuration occurs which is believed to effectively provide crosslinking points and which assists allowing for additional crosslinking of the carboxyalkyl polysaccharide upon further treatment as, for example, with heat- treatment. To allow for effective entanglement of individual segments of the carboxyalkyl polysaccharide with each other, the mixture is suitably allowed to form a stable, homogeneous mixture at equilibrium prior to additional treatment steps to ensure effective dissolution of the carboxyalkyl polysaccharide into the water. It will be appreciated that a non-water-soluble portion of the carboxyalkyl polysaccharide may exist that will typically not dissolve into water. For example, the retained crystalline areas of a crystalline-crosslinked polysaccharide will typically not dissolve in water while the non-crystalline areas typically will.

The carboxyalkyl polysaccharide is typically dissolved in a solvent comprising at least about 30 weight percent water, beneficially about 50 weight percent water, suitably about 75 weight percent water, and more suitably 100 weight percent water. When a co-solvent is employed with the water, other suitable solvents include methanol, ethanol, and acetone. However, the use or presence of such other, non-aqueous solvents may impede the formation of a homogeneous mixture such that the carboxyalkyl polysaccharide chains do not effectively dissolve into the solution and interpenetrate one another.

Crosslinking agents suitable for use in the present invention are generally water soluble. One suitable crosslinking agent is an organic compound having at least two functional groups or functionalities capable of reacting with the carboxyl, amino, or hydroxyl groups of a carboxyalkyl polysaccharide. It is desired that such an organic crosslinking agent be selected from the group consisting of diamines, polyamines, diols, and polyols and mixtures thereof; particularly from the group consisting of primary diols, primary polyols, primary diamines and primary polyamines and mixtures thereof. Of the diols and polyols, those possessing longer carbon chain lengths ($\geq 4$) are generally beneficial. Specifically, the crosslinking agent may be selected from the group consisting of chitosan glutamate, type A gelatin, diethylenetriamine, ethylene glycol, butylene glycol, polyvinyl alcohol, hyaluronic acid, polyethylene imine and their derivatives and mixtures thereof. Other suitable organic crosslinking agents include monochloroacetic acid, sodium chloroacetate, citric acid, butane tetracarboxylic acid, and amino acids such as aspartic acid, and mixtures thereof.

The presence of a crosslinking agent, particularly a diamine or polyamine, in certain processes of the present invention, may improve the initial Absorbency Under Load value of a carboxyalkyl polysaccharide according to the present invention when compared to an otherwise identical carboxyalkyl polysaccharide without a crosslinking agent in an otherwise similar process. Specifically, the carboxyalkyl polysaccharides prepared using a crosslinking agent may suitably have an initial Absorbency Under Load value of at least about 10 percent, and beneficially at least about 20 percent, greater than an otherwise identical carboxyalkyl polysaccharide without a crosslinking agent. The otherwise identical carboxyalkyl polysaccharide will have the same composition and be prepared in a process exactly like the carboxyalkyl polysaccharide of the present invention, except it will not comprise the crosslinking agent.

Another suitable crosslinking agent comprises a metal ion with more than two positive charges, such as $Al^{3+}$, $Fe^{3+}$, $Ce^{3+}$, $Ti^{4+}$, $Zr^{4+}$, and $Ce^{4+}$. Suitable metal ion crosslinking agents include those of the transition elements which generally have vacant d-orbitals. Suitable metal ion crosslinking agents include $AlCl_3$, $FeCl_3$, $Ce_2(SO_4)_3$, $Zr(NH_4)_4(CO_3)_4$ and $Ce(NH_4)_4(SO_4)_4 \cdot 2H_2O$, other well known metal ion compounds and mixtures thereof. Such metal ion crosslinking agents, when used with a carboxyalkyl polysaccharide, are believed to form ionic bonds with the carboxyl groups of the carboxyalkyl polysaccharide. Metal ions with only two positive charges, such as $Zn^{2+}$, $Ca^{2+}$, or $Mg^{2+}$, have generally been found to not provide sufficient crosslinking of the carboxyalkyl polysaccharide to result in the desired absorbent properties of the present invention. The crosslinking agent is generally used in an amount of from about 0.01 to about 20, beneficially of from about 0.05 to about 10, and suitably of from about 0.1 to about 5 weight percent, based on total weight of the carboxyalkyl polysaccharide present in the mixture.

Generally, the order of mixing the carboxyalkyl polysaccharide, water, and crosslinking agent is not critical when a crosslinking agent is used. As such, either the carboxyalkyl polysaccharide or the crosslinking agent may be added to the water and then the remaining material subsequently added, or all three materials may be added together at the same time. However, it may be beneficial, when using certain crosslinking agents, to first add the carboxyalkyl polysaccharide and water and then to add the crosslinking agent to the mixture. For example, if citric acid is used as the crosslinking agent, it may be beneficial that the carboxyalkyl polysaccharide and water first be mixed together and then the citric acid be added to the mixture.

In general, a crosslinking catalyst will not be needed, but may be beneficial, to assist in the crosslinking of the carboxyalkyl polysaccharides of the present invention. For example, if citric acid is used as the crosslinking agent, sodium hypophosphite is beneficially used as a crosslinking catalyst. Such crosslinking catalysts can be used in an amount of from about 0.01 to about 3.0 weight percent, suitably from about 0.1 to about 1.0 weight percent, based on the total weight of the carboxyalkyl polysaccharide used.

The aqueous mixture of a carboxyalkyl polysaccharide, water, and, optionally, a crosslinking agent, can generally be formed at any temperature at which the carboxyalkyl polysaccharide is soluble in the water. Generally, such temperatures will be within the range of from about 10° C. to about 100° C. As a general rule, it is suitable to form the mixture with agitation.

The aqueous mixture may be acidic (a pH of less than 7), neutral (a pH of 7), or basic (a pH greater than 7). If desired, the mixture can be acidified by the addition of an aqueous solution of an inorganic acid, such as hydrochloric acid, nitric acid, or the like, or an aqueous solution of an organic acid, such as acetic acid, or the like. Similarly, if it is desired to provide the aqueous mixture with a basic pH, a base such as an aqueous solution of sodium hydroxide, potassium hydroxide, ammonia, or the like can be added to the mixture.

The aqueous mixture will generally have a pH within the range of from about 2 to about 12, beneficially from about 4 to about 9, more beneficially from about 4 to about 7.5, and suitably from about 6 to about 7.5. The recovered carboxyalkyl polysaccharide will generally have the same pH as the mixture. However, when the carboxyalkyl polysaccharide is recovered by evaporative drying, the evaporative drying step generally tends to lower the pH of the recovered carboxyalkyl polysaccharide if the mixture is initially basic.

When the carboxyalkyl polysaccharide of the present invention is intended for use in personal care products, such as diapers, training pants, and feminine care products, it is typically desired that the carboxyalkyl polysaccharide have a generally neutral character. For this reason, it is generally beneficial that the aqueous mixture be formed with a generally neutral pH. If the aqueous mixture is formed with an acidic or basic pH, the recovered carboxyalkyl polysaccharide may be acidic or basic (respectively) but may be neutralized. A recovered carboxyalkyl polysaccharide which is acidic may be neutralized, for example, by contacting with a gaseous base such as ammonia. A recovered carboxyalkyl polysaccharide which is basic may be neutralized, for example, by contacting with an acidic gas such as carbon dioxide.

After forming a mixture of carboxyalkyl polysaccharide, water, and, optionally, a crosslinking agent, the carboxyalkyl polysaccharide is recovered from the mixture. Any method of recovering the carboxyalkyl polysaccharide from the mixture, without unacceptably deteriorating the absorption characteristics of the carboxyalkyl polysaccharide, is suitable for use in the present invention. Examples of such methods include evaporative drying, freeze drying, precipitation, critical point drying, and the like.

As used herein, recovery of the carboxyalkyl polysaccharide from the mixture is meant to represent that substantially all of the water is separated from the carboxyalkyl polysaccharide prior to additional treatment steps. It will be appreciated, however, that even after removal of substantially all of the water, a small amount of water may remain entrapped within the structure of the carboxyalkyl polysaccharide. The amount of water remaining entrapped within the structure of the carboxyalkyl polysaccharide will typically depend on the method and conditions under which the carboxyalkyl polysaccharide is recovered. Generally, less than about 15 weight percent, beneficially less than about 10 weight percent, and suitably less than about 5 weight percent, of the original amount of water in the mixture will remain entrapped within the recovered carboxyalkyl polysaccharide.

Suitably, the carboxyalkyl polysaccharide is recovered from the mixture with evaporative drying. As a general rule, the carboxyalkyl polysaccharide can be recovered by evaporative drying at a temperature within the range of from about 10° C. to about 100° C., suitably from about 50° C. to about 80° C. Naturally, higher temperatures can be employed if the mixture is placed under pressure. Lower temperatures can be employed if the mixture is placed under a vacuum.

Other methods of recovery include precipitation in which a precipitating agent, such as methanol, ethanol or acetone, is added to the mixture of carboxyalkyl polysaccharide, water, and, optionally, a crosslinking agent, to precipitate the carboxyalkyl polysaccharide out of the mixture. The carboxyalkyl polysaccharide can then be recovered by filtration. If precipitation is used to recover the carboxyalkyl polysaccharide, it may be desirable to wash the recovered carboxyalkyl polysaccharide to remove the precipitating agent.

Depending on the form in which the carboxyalkyl polysaccharide is recovered, it may be necessary or desirable to alter the form of the carboxyalkyl polysaccharide. For example, if evaporative drying is employed, the carboxyalkyl polysaccharide may be recovered in the form of a film or sheet. It may be desirable to comminute the film or sheet material into particles or flakes of material.

The form of the recovered carboxyalkyl polysaccharide desired will depend to a large extent on the use for which it is intended. When the carboxyalkyl polysaccharide is intended for use in absorbent personal care products, it is generally desired that the carboxyalkyl polysaccharide be in the form of a discrete particle, fiber or flake. When in the form of a particle, it is generally desired that the particle have a maximum cross-sectional dimension within the range from about 50 micrometers to about 2,000 micrometers, suitably within the range from about 100 micrometers to about 1,000 micrometers, beneficially within the range from about 300 micrometers to about 600 micrometers.

In general, the recovered carboxyalkyl polysaccharide may need to be heat-treated at an elevated temperature for a period of time. Such heat-treatment generally results in crosslinking or additionally crosslinking the carboxyalkyl polysaccharide in order to achieve the desired initial AUL value and aging stability as described herein.

However, if, for example, citric acid is used as the crosslinking agent and sodium hypophosphite is used as a crosslinking catalyst, it may be possible to prepare a carboxyalkyl polysaccharide which exhibits an effective initial AUL value and improved aging stability without the need for a further process step, such as heat-treatment, after recovery of the carboxyalkyl polysaccharide from the aqueous mixture.

In general, if heat-treatment is necessary, any combination of temperature and time which is effective in achieving a desired degree of crosslinking, without undesirable damage to the carboxyalkyl polysaccharide, so that the carboxyalkyl polysaccharide exhibits a desired initial AUL value and aging stability as described herein, is suitable for use in the present invention. As a general rule, when a crosslinking agent is used, the carboxyalkyl polysaccharide will be heat-treated at a temperature within the range from about 50° C. to about 250° C., beneficially from about 80° C. to about 250° C., more beneficially from about 100° C. to about 200° C., and suitably from about 100° C. to about 160° C. The higher the temperature employed, the shorter the period of time generally necessary to achieve the desired degree of crosslinking. It has been found that if very high temperatures are used with an effective length of time, such as a temperature between about 200° C. and about 250° C. for a length of time between about 50 and about 90 seconds, an effective initial AUL value and sufficient aging stability may be achieved for a carboxyalkyl polysaccharide without the use of a crosslinking agent. Generally, the heat-treating process will extend over a time period within the range of from about 1 minute to about 600 minutes, beneficially from about 2 minutes to about 200 minutes, and suitably from about 5 minutes to about 100 minutes.

By providing an aqueous mixture of carboxyalkyl polysaccharide, water and, optionally, a crosslinking agent, with an acidic character, the time necessary to effect the crosslinking may be shortened. Without intending to be bound hereby, this is believed to be because a weakly acidic carboxyalkyl polysaccharide will generally have more free carboxylic acid groups present so that more ester linkage bonds may be formed even during a relatively low temperature heat-treatment. Providing the aqueous mixture with a slightly basic character tends to lengthen the time of the crosslinking process, at a given temperature, compared to a slightly acidic or neutral mixture. Nonetheless, similar general absorptive properties can generally be achieved with either an acidic, neutral, or basic aqueous mixture. In some instances, it may be desired to provide the aqueous mixture and the recovered carboxyalkyl polysaccharide with an acidic character in order to lower the temperature or shorten the time of the heat-treatment. In this instance, the carboxyalkyl polysaccharide may be neutralized after the heat-treatment step.

The heat-treating process generally causes the carboxyalkyl polysaccharide to crosslink or additionally crosslink and become generally water swellable and water insoluble. Without intending to be bound hereby, it is believed that the heat-treating process causes the carboxyalkyl polysaccharide to undergo a degree of self-crosslinking, not related to the presence of a crosslinking agent, through the formation of ester linkages. This self-crosslinking is in addition to any crosslinking caused by the presence of a crosslinking agent. Further, when the crosslinking agent is a diamine or polyamine, it is believed that crosslinking occurs through amidation of the carboxyl group through the formation of an ammonia salt. Esterification, through a self-crosslinking process, is believed to occur primarily under a weakly acidic, neutral, or slightly basic condition. Esterification, through a self-crosslinking process, is not believed to proceed to a significant degree under relatively basic conditions. Crosslinking due to the crosslinking agent may occur under both acidic and basic conditions. Thus, the presence of the crosslinking agent allows for crosslinking to occur over a broad pH range.

There is generally an optimum degree or amount of crosslinking of a particular carboxyalkyl polysaccharide that optimizes the initial Absorbency Under Load value and aging stability of the particular modified polysaccharide. If too little crosslinking occurs, the carboxyalkyl polysaccharide may possess a relatively low initial Absorbency Under Load value due to a lack of gel strength. If too much crosslinking occurs, the carboxyalkyl polysaccharide may similarly have a relatively low initial Absorbency Under Load value due to the inability of the carboxyalkyl polysaccharide to absorb liquid.

Those skilled in the art will recognize that the presence of crosslinks formed by esterification or amidation can be detected through various analytical techniques. For example, infrared spectroscopy and nuclear magnetic resonance can be used to verify the presence of ester and amide crosslinks.

In another aspect, the present invention relates to a water-swellable, water-insoluble carboxyalkyl polysaccharide characterized in that the carboxyalkyl polysaccharide possesses crosslinks formed by esterification and amidation. Such a carboxyalkyl polysaccharide is suitably formed by the methods described above. Nonetheless, the described methods are not intended to be the exclusive methods by which such a carboxyalkyl polysaccharide can be formed.

TEST METHODS

Absorbency Under Load

The Absorbency Under Load (AUL) is a test which measures the ability of an absorbent material to absorb a liquid (such as a 0.9 weight percent solution of sodium chloride in distilled water) while under an applied load or restraining force.

Referring to FIG. 1, the apparatus and method for determining AUL will be described. Shown is a perspective view of the apparatus in position during a test. Shown is a laboratory jack 1 having an adjustable knob 2 for raising and lowering the platform 3. A laboratory stand 4 supports a spring 5 connected to a modified thickness meter probe 6, which passes through the housing 7 of the meter, which is rigidly supported by the laboratory stand. A plastic sample cup 8, which contains the superabsorbent material sample to be tested, has a liquid-permeable bottom and rests within a Petri dish 9, which contains the saline solution to be absorbed. A weight 10 rests on top of a spacer disc (not visible) resting on top of the superabsorbent material sample (not visible).

The sample cup consists of a plastic cylinder having a 1 inch inside diameter and an outside diameter of 1.25 inches. The bottom of the sample cup is formed by adhering a 100 mesh metal screen having 150 micron openings to the end of the cylinder by heating the screen above the melting point of the plastic and pressing the plastic cylinder against the hot screen to melt the plastic and bond the screen to the plastic cylinder.

The modified thickness meter used to measure the expansion of the sample while absorbing the saline solution is a Mitutoyo Digimatic Indicator, IDC Series 543, Model 543-180, having a range of 0–0.5 inch and an accuracy of 0.00005 inch (Mitutoyo Corporation, 31-19, Shiba 5-chome, Minato-ku, Tokyo 108, Japan). As supplied from Mitutoyo Corporation, the thickness meter contains a spring attached to the probe within the meter housing. This spring is removed to provide a free-falling probe which has a downward force of about 27 grams. In addition, the cap over the top of the probe, located on the top of the meter housing, is also removed to enable attachment of the probe to the suspension spring 5 (available from McMaster-Carr Supply Co., Chicago, Ill. Item No. 9640K41), which serves to counter or reduce the downward force of the probe to about 1 gram, ±0.5 gram. A wire hook can be glued to the top of the probe for attachment to the suspension spring. The bottom tip of the probe is also provided with an extension needle (Mitutoyo Corporation, Part No. 131279) to enable the probe to be inserted into the sample cup.

To carry out the test, a 0.160 gram sample of the absorbent material, which has been sieved to a particle size between 300 and 600 microns, is placed into the sample cup. The sample is then covered with a plastic spacer disc, weighing 4.4 grams, which is slightly smaller than the inside diameter of the sample cup and serves to protect the sample from being disturbed during the test. The 100 gram weight is then placed on top of the spacer disc, thereby applying a load of about 0.3 pound per square inch. The sample cup is placed in the Petri dish on the platform and the laboratory jack raised up until it contacts the tip of the probe. The meter is zeroed. A sufficient amount of saline solution is added to the Petri dish (50–100 milliliters) to begin the test. The distance the weight is raised by the expanding sample as it absorbs the saline solution is measured by the probe. This distance, multiplied by the cross-sectional area inside the sample cup, is a measure of the expansion volume of the sample due to absorption. Factoring in the density of the saline solution and the weight of the sample, the amount of saline solution absorbed is readily calculated. The weight of saline solution absorbed after about 60 minutes is the AUL value expressed as grams saline solution absorbed per gram of absorbent. If desired, the readings of the modified thickness meter can be continuously inputted to a computer (Mitutoyo Digimatic Miniprocessor DP-2 DX) to make the calculations and provide AUL readings. As a cross-check, the AUL can also be determined by determining the weight difference between the sample cup before and after the test, the weight difference being the amount of solution absorbed by the sample.

EXAMPLES

Example 1

Two sodium carboxymethyl celluloses (CMC) commercially available from the Aqualon Company under the trade designation AQUALON® Cellulose Gum CMC-7HCF or CMC-9H4F are provided. The CMC-7HCF has an average degree of substitution of about 0.7 and a viscosity in a 1 percent aqueous solution at 25° C. of about 1000–2800 centipoise. The CMC-9H4F has an average degree of substitution of about 0.9 and a viscosity in a 1 percent aqueous solution at 25° C. of about 2500–6000 centipoise. Each carboxymethyl cellulose is individually dissolved in distilled water to form a solution containing 2 weight percent carboxymethyl cellulose based on total solution weight. A crosslinking agent is dissolved in water to form a solution containing 0.5 weight percent of the crosslinking agent based on total solution weight. The crosslinking agents employed are chitosan glutamate, commercially available from Protan Biopolymer A/S, Norway, under the trade designation Sea Cure G; 1,4-butylene glycol, commercially available from the Aldrich Chemical Company; polyethylene imine (molecular weight 50,000–100,000) commercially available from Polysciences, Inc.; sodium salt of hyaluronic acid commercially available from Sigma; Type A gelatin commercially available from the Aldrich Chemical Company under the trade designation 300 Bloom; and diethylene triamine commercially available from the Aldrich Chemical Company. The aqueous solution containing the crosslinking agent is then added to the individual aqueous solutions containing the carboxymethyl cellulose to provide various concentrations of crosslinking agent based on total weight of the carboxymethyl cellulose present in the aqueous solution. The resulting mixtures containing water, carboxymethyl cellulose, and crosslinking agent are then thoroughly mixed. The carboxymethyl cellulose is recovered from the solution by evaporative drying at 80° C. in a Blue M air-convection oven. After drying, the recovered carboxymethyl cellulose is ground into granules in a blender and heat-treated at various times and temperatures in an oven. Various combinations of carboxymethyl cellulose, crosslinking agent, concentration of crosslinking agent, heat-treatment temperature and heat-treatment time are made. The initial Absorbency Under Load values of the various carboxymethyl celluloses so prepared are measured. The exact combination of carboxymethyl cellulose and crosslinking agent and its initial AUL value are set forth in Table 1. Similarly, control samples of the carboxymethyl cellulose CMC-7HCF and CMC-9H4F are tested for AUL values. These results are also set forth in Table 1.

As can be seen from reference to Table 1, the method according to the present invention significantly increases the initial Absorbency Under Load value of the starting carboxymethyl cellulose materials. All of the crosslinking agents employed are effective to increase the initial Absorbency Under Load values. Further, it is seen that the crosslinking agents are effective over a range of concentrations.

Example 2

The chitosan glutamate aqueous solution employed in Example 1 is weakly acidic. In order to evaluate the effect of pH, a basic crosslinker (diethylenetriamine, commercially available from the Aldrich Chemical Company), is used. Again, a carboxymethyl cellulose (CMC-7HCF) is dissolved in distilled water to form a 2 weight percent aqueous solution. The diethylenetriamine is dissolved in water to form a 0.5 weight percent aqueous solution. The aqueous

TABLE 1

| Sample No. | CMC | Crosslinking Agent | Crosslinking Agent Concentration[1] | Treatment Temp. (°C.) | Treatment Time (min) | Initial AUL Value (g/g) |
|---|---|---|---|---|---|---|
| 1* | CMC-7HCF | None | — | — | — | 4.9 |
| 2* | CMC-7HCF | None | — | 150 | 35 | 22.3 |
| 3* | CMC-7HCF | Chitosan Glutamate | 0.3 | — | — | 7.1 |
| 4 | CMC-7HCF | Chitosan Glutamate | 0.3 | 140 | 60 | 22.6 |
| 5 | CMC-7HCF | Chitosan Glutamate | 0.3 | 140 | 70 | 29.2 |
| 6 | CMC-7HCF | Chitosan Glutamate | 0.3 | 140 | 75 | 31.8 |
| 7 | CMC-7HCF | Chitosan Glutamate | 0.3 | 140 | 90 | 22.9 |
| 8* | CMC-7HCF | Chitosan Glutamate | 0.5 | — | — | 4.8 |
| 9 | CMC-7HCF | Chitosan Glutamate | 0.5 | 125 | 60 | 13.2 |
| 10 | CMC-7HCF | Chitosan Glutamate | 0.5 | 140 | 20 | 14.4 |
| 11 | CMC-7HCF | Chitosan Glutamate | 0.5 | 140 | 30 | 22.2 |
| 12 | CMC-7HCF | Chitosan Glutamate | 0.5 | 140 | 35 | 24.3 |
| 13 | CMC-7HCF | Chitosan Glutamate | 0.5 | 140 | 40 | 21.9 |
| 14* | CMC-7HCF | Chitosan Glutamate | 1.0 | — | — | 6.0 |
| 15 | CMC-7HCF | Chitosan Glutamate | 1.0 | 125 | 60 | 15.6 |
| 16 | CMC-7HCF | Chitosan Glutamate | 1.0 | 125 | 90 | 17.6 |
| 17 | CMC-7HCF | Chitosan Glutamate | 1.0 | 125 | 110 | 19.8 |
| 18 | CMC-7HCF | Chitosan Glutamate | 1.0 | 125 | 120 | 18.4 |
| 19* | CMC-9H4F | None | — | — | — | 6.5 |
| 20* | CMC-9H4F | Chitosan Glutamate | 0.5 | — | — | 7.1 |
| 21 | CMC-9H4F | Chitosan Glutamate | 0.5 | 130 | 80 | 22.4 |
| 22 | CMC-9H4F | Chitosan Glutamate | 0.5 | 130 | 90 | 27.1 |
| 23 | CMC-9H4F | Chitosan Glutamate | 0.5 | 140 | 30 | 24.4 |
| 24 | CMC-9H4F | Chitosan Glutamate | 0.5 | 150 | 30 | 21.7 |
| 25 | CMC-7HCF | 1,4-butylene glycol | 0.5 | 150 | 40 | 19.7 |
| 26 | CMC-7HCF | 1,4-butylene glycol | 0.5 | 150 | 50 | 25.5 |
| 27 | CMC-7HCF | 1,4-butylene glycol | 0.5 | 150 | 60 | 25.8 |
| 28 | CMC-7HCF | 1,4-butylene glycol | 0.5 | 150 | 80 | 22.9 |
| 29 | CMC-7HCF | 1,4-butylene glycol | 1.0 | 150 | 30 | 22.2 |
| 30 | CMC-7HCF | 1,4-butylene glycol | 1.0 | 150 | 50 | 25.5 |
| 31 | CMC-7HCF | 1,4-butylene glycol | 1.0 | 150 | 70 | 25.8 |
| 32 | CMC-7HCF | 1,4-butylene glycol | 1.0 | 150 | 80 | 22.9 |
| 33 | CMC-7HCF | polyethylene imine | 1.0 | 150 | 10 | 13.2 |
| 34 | CMC-7HCF | polyethylene imine | 1.0 | 150 | 20 | 17.3 |
| 35 | CMC-7HCF | polyethylene imine | 1.0 | 150 | 30 | 15.7 |
| 36 | CMC-7HCF | polyethylene imine | 2.0 | 150 | 20 | 17.3 |
| 37 | CMC-7HCF | polyethylene imine | 2.0 | 150 | 30 | 21.5 |
| 38 | CMC-7HCF | polyethylene imine | 2.0 | 150 | 50 | 15.7 |
| 39* | CMC-7HCF | hyaluronic acid | 0.5 | — | — | 6.3 |
| 40 | CMC-7HCF | hyaluronic acid | 0.5 | 150 | 30 | 23.0 |
| 41 | CMC-7HCF | hyaluronic acid | 0.5 | 150 | 40 | 27.9 |
| 42 | CMC-7HCF | hyaluronic acid | 0.5 | 150 | 45 | 28.3 |
| 43 | CMC-7HCF | hyaluronic acid | 0.5 | 150 | 50 | 27.9 |
| 44 | CMC-7HCF | gelatin | 2.0 | 125 | 40 | 16.3 |
| 45 | CMC-7HCF | gelatin | 2.0 | 125 | 50 | 19.7 |
| 46 | CMC-7HCF | gelatin | 2.0 | 125 | 60 | 17.8 |
| 47 | CMC-7HCF | diethylene triamine | 2.0 | 125 | 60 | 8.6 |
| 48 | CMC-7HCF | diethylene triamine | 2.0 | 125 | 105 | 17.2 |

*Not an example of the present invention
[1]Weight percent based on total weight carboxymethyl cellulose solution of diethylenetriamine is then added to the aqueous solution of carboxymethyl cellulose to provide a diethylenetriamine concentration of 2.0 weight percent based on total weight of the carboxymethyl cellulose present in the aqueous solution. The carboxymethyl cellulose is then recovered by evaporative drying and comminuted into particles as described in Example 1. A comparison material is prepared by dissolving carboxymethyl cellulose (CMC-7HCF) in distilled water to form a 2 weight percent solution. To the aqueous solution of carboxymethyl cellulose is then added 0.004 weight percent sodium hydroxide. The comparison carboxymethyl cellulose is recovered and comminuted into particles as described in Example 1. Both samples are then heated at various temperatures for 30 minutes. The resulting polymers are tested for initial Absorbency Under Load. The results of the testing are set forth in Table 2.

TABLE 2

| Sample No. | Composition | Treatment Temp (°C.) | Treatment Time (min.) | AUL Value (g/g) |
|---|---|---|---|---|
| 49 | CMC/diethylenetriamine | 80 | 30 | 6.2 |
| 50 | CMC/diethylenetriamine | 110 | 30 | 6.2 |
| 51 | CMC/diethylenetriamine | 120 | 30 | 6.5 |
| 52 | CMC/diethylenetriamine | 130 | 30 | 7.7 |
| 53 | CMC/diethylenetriamine | 140 | 30 | 13.1 |
| 54 | CMC/diethylenetriamine | 150 | 30 | 17.9 |
| 55 | CMC/diethylenetriamine | 160 | 30 | 15.9 |
| 56 | CMC/diethylenetriamine | 170 | 30 | 14.0 |
| 57* | CMC/sodium hydroxide | 80 | 30 | 6.1 |
| 58* | CMC/sodium hydroxide | 110 | 30 | 6.0 |
| 59* | CMC/sodium hydroxide | 120 | 30 | 5.6 |
| 60* | CMC/sodium hydroxide | 130 | 30 | 6.0 |
| 61* | CMC/sodium hydroxide | 140 | 30 | 5.9 |
| 62* | CMC/sodium hydroxide | 150 | 30 | 5.3 |
| 63* | CMC/sodium hydroxide | 160 | 30 | 5.4 |
| 64* | CMC/sodium hydroxide | 180 | 30 | 4.3 |

*Not an example of the present invention.

As can be seen from reference to Table 2, the carboxymethyl cellulose without a crosslinking agent, under basic conditions, exhibits no improvement in initial Absorbency Under Load values through the heat-treating step. In contrast, the carboxymethyl cellulose containing the basic crosslinker, diethylene triamine, is seen to exhibit an improvement in initial AUL value as a result of the heat-treating step. This is believed to indicate that a self-crosslinking of the carboxymethyl cellulose does not readily occur at relatively basic pH.

Example 3

Sample Nos. 65–71 are prepared by forming an aqueous solution containing 2 weight percent of carboxymethyl cellulose (CMC-7HCF). To the aqueous solution is added an amount of sodium hydroxide sufficient to bring the pH of the solution to 9. No crosslinking agent is present in the solution. The carboxymethyl cellulose is then, according to the method of Example 1, recovered, comminuted, heat-treated at 150° C. for various times, and tested for Absorbency Under Load.

Sample Nos. 72–77 are prepared by forming an aqueous solution comprising 2 weight percent carboxymethyl cellulose (CMC-7HCF). To the solution is then added 0.5 weight percent chitosan glutamate in the manner set forth in Example 1. The solution is found to have a pH of about 7.4. The carboxymethyl cellulose is then, according to the method of Example 1, recovered, comminuted, heat-treated at 150° C. for various times and tested for initial Absorbency Under Load.

Sample Nos. 78–103 are prepared in the same manner as Sample Nos. 72–77, except sodium hydroxide is added to the aqueous solution containing carboxymethyl cellulose and chitosan glutamate prior to recovery. The amount of sodium hydroxide added is sufficient to bring the pH of the solution to 9.2, 10.1, or 10.9. The carboxymethyl cellulose is then, according to the method of Example 1, recovered, comminuted, heat-treated at 150° C. for various times and tested for initial Absorbency Under Load.

The results of this testing (sample nos. 65–103) are set forth in Table 3.

TABLE 3

| Sample Value No. | Crosslinking Agent | pH | Treatment Temp (°C.) | Treatment Time (min) | Initial AUL (g/g) |
|---|---|---|---|---|---|
| 65* | None | 9.0 | — | — | 4.9 |
| 66* | None | 9.0 | 150 | 30 | 6.9 |
| 67* | None | 9.0 | 150 | 50 | 6.9 |
| 68* | None | 9.0 | 150 | 80 | 6.6 |
| 69* | None | 9.0 | 150 | 110 | 6.5 |
| 70* | None | 9.0 | 150 | 150 | 6.6 |
| 71* | None | 9.0 | 150 | 180 | 6.4 |
| 72* | Chitosan glutamate | 7.4 | — | — | 4.8 |
| 73 | Chitosan glutamate | 7.4 | 150 | 15 | 11.1 |
| 74 | Chitosan glutamate | 7.4 | 150 | 22 | 19.6 |
| 75 | Chitosan glutamate | 7.4 | 150 | 30 | 22.4 |
| 76 | Chitosan glutamate | 7.4 | 150 | 45 | 20.2 |
| 77 | Chitosan glutamate | 7.4 | 150 | 60 | 17.8 |
| 78* | Chitosan glutamate | 9.2 | — | — | 4.9 |
| 79 | Chitosan glutamate | 9.2 | 150 | 15 | 7.3 |
| 80 | Chitosan glutamate | 9.2 | 150 | 30 | 10.6 |
| 81 | Chitosan glutamate | 9.2 | 150 | 45 | 19.5 |
| 82 | Chitosan glutamate | 9.2 | 150 | 60 | 23.5 |
| 83 | Chitosan glutamate | 9.2 | 150 | 70 | 24.1 |
| 84 | Chitosan glutamate | 9.2 | 150 | 80 | 23.2 |
| 85 | Chitosan glutamate | 9.2 | 150 | 120 | 25.0 |
| 86 | Chitosan glutamate | 9.2 | 150 | 150 | 26.5 |
| 87 | Chitosan glutamate | 9.2 | 150 | 180 | 27.4 |
| 88 | Chitosan glutamate | 9.2 | 150 | 240 | 21.6 |
| 89* | Chitosan glutamate | 10.1 | — | — | 4.9 |
| 90 | Chitosan glutamate | 10.1 | 150 | 30 | 7.1 |
| 91 | Chitosan glutamate | 10.1 | 150 | 60 | 8.3 |
| 92 | Chitosan glutamate | 10.1 | 150 | 120 | 16.1 |
| 93 | Chitosan glutamate | 10.1 | 150 | 150 | 19.3 |
| 94 | Chitosan glutamate | 10.1 | 150 | 180 | 21.3 |
| 95 | Chitosan glutamate | 10.1 | 150 | 210 | 20.5 |
| 96 | Chitosan glutamate | 10.1 | 150 | 240 | 23.0 |
| 97* | Chitosan glutamate | 10.9 | — | — | 4.9 |
| 98 | Chitosan glutamate | 10.9 | 150 | 60 | 7.2 |
| 99 | Chitosan glutamate | 10.9 | 150 | 110 | 9.6 |
| 100 | Chitosan glutamate | 10.9 | 150 | 120 | 12.3 |
| 101 | Chitosan glutamate | 10.9 | 150 | 150 | 13.8 |
| 120 | Chitosan glutamate | 10.9 | 150 | 180 | 15.8 |
| 103 | Chitosan glutamate | 10.9 | 150 | 240 | 19.4 |

*Not an example of the present invention

As can be seen from reference to and Table 3, basic carboxymethyl cellulose containing no crosslinking agent (Sample Nos. 65–71) exhibits no significant improvement in initial Absorbency Under Load values as a result of heat-treatment. In contrast, Sample Nos. 72–103 show improvements in initial AUL values. It is seen that, at a lower pH, the heat-treatment time required to optimize initial AUL values is shorter than at a higher pH.

Example No. 4

A carboxymethyl cellulose commercially available from Aqualon Company under the trade designation AQUALON™ Cellulose Gum CMC-7L is provided. This carboxymethyl cellulose has a relatively low molecular weight exhibiting a viscosity in a 2 percent aqueous solution at 25° C. of about 25–50 centipoise. Sample No. 104 (comparative)

is prepared by forming an aqueous solution containing 2 weight percent of the carboxymethyl cellulose (CMC-7L). The carboxymethyl cellulose is recovered and dried as described in Example 1. The material is found to have an initial Absorbency Under Load value of 2.1. Sample No. 105 (comparative) is prepared in the same manner as Sample No. 104 with the exception that, after recovery, the material is comminuted and heat-treated at 170° C. for 160 minutes. The resultant material is found to have an initial Absorbency Under Load value of 8.6. Neither material contains a crosslinking agent.

Sample No. 106 is prepared by forming an aqueous solution containing 2 weight percent of the carboxymethyl cellulose (CMC-7L). To the aqueous solution is added 1 weight percent chitosan glutamate in the manner set forth in Example 1. The carboxymethyl cellulose is then recovered and comminuted as set forth in Example 1. The resultant material is then heat-treated at 170° C. for two hours. The resulting material is found to have an initial Absorbency Under Load value of about 14.7.

From the above, it is seen that the presence of the chitosan glutamate crosslinking agent greatly improves the initial Absorbency Under Load value of low molecular weight carboxymethyl cellulose compared to nonheat-treated materials and heat-treated materials not containing a crosslinking agent.

Example No. 5

To determine the aging characteristics of absorbent material according to the present invention and comparative absorbent material, the following samples are provided:

Sample No. 107 is prepared similarly to Sample No. 2.

Sample No. 108 is prepared similarly to Sample Nos. 25–28, except the material is heated at 150° C. for 70 minutes.

Sample No. 109 is prepared similarly to Sample No. 42. A different initial AUL value is obtained.

Sample No. 110 is prepared similarly to Sample No. 24, except the material is heated for 20 minutes.

Sample No. 111 is prepared according to the method of Example 1 employing ethylene glycol as the crosslinking agent. The material is heat-treated at 170° C. for 30 minutes.

Sample Nos. 107–111 were placed in a temperature and humidity controlled environment. The temperature was maintained at 24° C. and the humidity was maintained at 30 percent relative humidity. The samples were tested for AUL value at various points throughout the 60-day aging study. The results are set forth in Table 4. The reported "AUL retention" is the 60-day AUL reported as a percentage of day 0 (initial) AUL. That is, 60-day AUL divided by 0 day AUL.

TABLE 4

| Sample No. | AUL Value (g/g) | | | | | | | AUL Retention |
|---|---|---|---|---|---|---|---|---|
| | 0 days | 4 days | 8 days | 12 days | 26 days | 50 days | 60 days | |
| 107* | 22.3 | 17.0 | 14.2 | 17.7 | 12.1 | 7.6 | 7.7 | 34.5 |
| 108 | 25.9 | 20.9 | 22.5 | 22.4 | 20.9 | 20.9 | 21.5 | 83.1 |
| 109 | 24.5 | 22.7 | 21.8 | 21.8 | 19.3 | 18.1 | 18.8 | 76.7 |
| 110 | 21.8 | 20.4 | 20.9 | 19.7 | 17.0 | 15.1 | 16.2 | 74.3 |
| 111 | 21.5 | 20.1 | 17.9 | 18.5 | 16.3 | 16.1 | 15.8 | 73.5 |

*Not an example of the present invention

As can be seen from reference to Table 4, while heat-treatment alone can, in the absence of a crosslinking agent, provide an As can be seen from reference to Table 4, while heat-treatment alone can, in the absence of a crosslinking agent, provide an acceptable initial AUL, the 60-day AUL retention is only 34.5 percent (Sample No. 107). The presence of a crosslinking agent according to the present invention provides an improved 60-day AUL retention (Sample Nos. 108–111).

Example 6

The use of polyvalent metal ions is evaluated for use as crosslinking agents. A carboxymethyl cellulose is dissolved in distilled water to form solutions containing 2 weight percent carboxymethyl cellulose based on total solution weight. A metal ion crosslinking agent is dissolved in water to form a solution. The aqueous solution containing the metal ion crosslinking agent is then added to individual aqueous solutions containing the carboxymethyl cellulose to provide various concentrations of crosslinking agent based on total weight of the carboxymethyl cellulose present in the aqueous solution. The resulting mixtures containing water, carboxymethyl cellulose, and crosslinking agent are then thoroughly mixed. The carboxymethyl cellulose is recovered from the solution by evaporative drying at between about 30° C. and about 50° C. After drying, the recovered carboxymethyl cellulose is ground and screened into 300 to 600 micrometer granules. The granules are then heat-treated at various times and temperatures in an oven. Various combinations of carboxymethyl cellulose, metal ion crosslinking agent, concentration of crosslinking agent, heat-treatment temperature and heat-treatment time are made. The initial Absorbency Under Load values, as well as the aging characteristics, of the various carboxymethyl celluloses so prepared are measured. For the aging characteristics testing, ambient conditions of about 23° C. and between about 30 to about 60 percent relative humidity are used. The exact combination of carboxymethyl cellulose and crosslinking agent and its AUL value are set forth in Table 5. Similarly, control samples of the carboxymethyl cellulose are tested for AUL values. These results are also set forth in Table 5.

TABLE 5

| Sample No. | CMC | Crosslinking Agent | Crosslinking Agent Concentration[1] | Treatment Temp. (°C.) | Treatment Time (min) | AUL Value (g/g) 0 days | AUL Value (g/g) 200 days |
|---|---|---|---|---|---|---|---|
| 112* | CMC-7H4F | — | — | — | — | 7.1 | — |
| 113* | CMC-7H4F | — | — | 140 | 90 | 22.7 | 10.4 |
| 114 | CMC-7H4F | $AlCl_3$ | 0.5 | — | — | 19.0 | 19.2 |
| 115 | CMC-7H4F | $AlCl_3$ | 0.5 | 110 | 90 | 24.1 | 20.4 |
| 116 | CMC-7H4F | $FeCl_3$ | 0.6 | — | — | 8.7 | — |
| 117 | CMC-7H4F | $FeCl_3$ | 0.6 | 115 | 25 | 22.4 | 14.7 |
| 118 | CMC-7H4F | $Ce(NH_4)_4(SO_4)_4 \cdot 2H_2O$ | 1.78 | — | — | 8.7 | — |
| 119 | CMC-7H4F | $Ce(NH_4)_4(SO_4)_4 \cdot 2H_2O$ | 1.78 | 115 | 25 | 21.3 | 15.8 |
| 120* | CMC-7H4F | $ZnCl_2$ | 0.77 | — | — | 7.0 | — |
| 121* | CMC-7H4F | $ZnCl_2$ | 0.77 | 130 | 120 | 23.5 | 10.3 |
| 122* | CMC-7H4F | $CaCl_2$ | 0.63 | — | — | 7.5 | — |
| 123* | CMC-7H4F | $CaCl_2$ | 0.63 | 130 | 120 | 23.5 | 8.5 |
| 124* | CMC-7H4F | $MgCl_2$ | 0.53 | — | — | 7.6 | — |
| 125* | CMC-7H4F | $MgCl_2$ | 0.53 | 130 | 120 | 23.3 | 8.2 |

*Not an example of the present invention
[1]Weight percent based on total weight carboxymethyl cellulose Sample No. 126 is prepared similarly to Sample No. 114 and placed in a temperature and humidity controlled environment. The temperature is maintained at about 23° C. and the humidity is maintained at about 100 percent relative humidity. The samples are tested for AUL value at various points throughout an aging study. The results are set forth in Table 6.

TABLE 6

| Sample No. | AUL Value (g/g) 0 days | 10 days | 20 days | 30 days | 40 days |
|---|---|---|---|---|---|
| 126 | 19.0 | 15.6 | 16.6 | 16.4 | 15.3 |

Carboxymethyl cellulose (Aqualon CMC-7H4F) is dissolved in distilled water to give 2 weight percent solutions and mixed using a commercial Hobart mixer run at low to medium speed. Various amounts of ammonium zirconium carbonate (AZC) is added to the solutions. The solutions are dried at 50° C. overnight in a convection oven. After grinding and sieving, the samples are tested for AUL values wherein the post heat-treatment time is 0 minutes. A post heat-treatment (curing), at a temperature of 110° C. for various lengths of time, is used to additionally crosslink the samples. The samples are again tested for AUL values. The results are set forth in Table 7.

medium speed. For Samples 133–141, 3 weight percent ammonium zirconium carbonate, based on the weight of carboxymethyl cellulose, is added to the solutions. For Sample 142, 1 weight percent ammonium zirconium carbonate, based on the weight of carboxymethyl cellulose, is added to the solution. Sample 133 is dried at 50° C. for two days in a convection oven. Samples 134–135 are dried at 50° C. for four days in a convection oven. Samples 136–141 are dried at 80° C. for four days in a convection oven. Sample 142 is dried at 80° C. for two days in a convection oven and then post heat-treated for 20 minutes at 80° C. After grinding and sieving, the samples are placed in a temperature and humidity controlled environment. The temperature is maintained at about 23° C. and the humidity is maintained at about 100 percent relative humidity. The samples are tested for AUL values at various points throughout an aging study. The results are set forth in Table 8.

TABLE 8

| Sample | AUL Value (g/g) | | | | | | |
|---|---|---|---|---|---|---|---|
| | 0 days | 9 days | 10 days | 11 days | 13 days | 20 days | 22 days |
| 133 | 19.9 | — | — | 16.7 | — | 17.6 | — |
| 134 | 20.8 | — | — | — | 18.2 | — | 19.9 |
| 135 | 15.6 | — | — | — | 17.7 | — | 18.5 |
| 136 | 21.0 | — | 20.3 | — | — | 19.9 | — |
| 137 | 20.8 | — | 19.8 | — | — | 19.7 | — |

TABLE 7

| Sample No. | AZC/CMC Wt. ratio | Curing Time (mins) | | | | | | | | | | |
|---|---|---|---|---|---|---|---|---|---|---|---|---|
| | | 0 | 10 | 20 | 30 | 40 | 50 | 60 | 80 | 100 | 160 | 200 |
| 127* | 0/100 | 6.5 | — | — | 6.7 | — | — | 6.5 | — | 6.6 | — | 6.9 |
| 128* | 0.5/100 | 9.5 | — | — | — | — | — | — | — | — | — | — |
| 129* | 1/100 | 13.0 | — | — | — | — | — | — | — | — | — | — |
| 130 | 2/100 | 20.5 | 20.1 | 20.6 | 20.8 | 20.6 | — | 20.8 | 21.0 | 21.2 | 19.2 | 17.5 |
| 131 | 3/100 | 23.0 | — | 21.6 | 24.1 | — | 21.4 | — | 19.0 | — | 17.6 | — |
| 132 | 4/100 | 21.4 | — | 18.1 | 18.7 | — | 17.3 | — | 16.3 | — | 13.6 | — |

*Not an example of the present invention

Carboxymethyl cellulose (Aqualon CMC-7H4F) is dissolved in distilled water to give 2 weight percent solutions and mixed using a commercial Hobart mixer run at low to

TABLE 8-continued

| Sample | AUL Value (g/g) | | | | | | |
|---|---|---|---|---|---|---|---|
| | 0 days | 9 days | 10 days | 11 days | 13 days | 20 days | 22 days |
| 138 | 21.4 | — | — | — | 18.5 | — | 16.8 |
| 139 | 19.7 | — | — | — | 18.1 | — | 19.3 |
| 140 | 18.4 | — | — | — | 18.4 | — | 19.1 |
| 141 | 18.4 | — | — | — | 18.3 | — | 19.4 |
| 142 | 20.1 | 16.8 | — | — | — | 17.1 | — |

Carboxymethyl cellulose [prepared from a cellulose pulp prepared using a Kraft process from a northern hardwood, wherein sodium hydroxide is used in a caustic treatment after bleaching; and wherein the cellulose pulp exhibits a viscosity of about 43 centipoise and a degree of polymerization (number average) of about 2023; and wherein the carboxymethyl cellulose has a degree of substitution in the range of from about 0.7 to about 0.9] is dissolved in distilled water to give 2 weight percent solutions and mixed using a commercial Hobart mixer run at low to medium speed. Ferric chloride (0.6 weight percent, based on weight of the CMC) is added to the solutions. The solutions are dried at 80° C. overnight in a convection oven. After grinding and sieving, the samples are tested for AUI values. A post heat-treatment, at a temperature of 140° C. for various lengths of time, is used to additionally crosslink the samples. The samples are again tested for AUL values. The results are set forth in Table 9.

TABLE 9

| Sample No. | AUL Value (g/g) | | | | | | | |
|---|---|---|---|---|---|---|---|---|
| | 0 Mins. | 5 Mins. | 10 Mins. | 20 Mins. | 25 Mins. | 30 Mins. | 40 Mins. | 50 Mins. |
| 143 | 10.6 | 12.4 | 19.9 | 21.5 | 23.1 | 20.2 | 18.9 | 17.4 |

Sample No. 144 represents the material from Table 9 wherein the CMC is post heat-treated at a temperature of 140° C. for 25 minutes. Sample No. 145 represents the material from Table 9 wherein the CMC is post heat-treated at a temperature of 140° C. for 30 minutes. These samples are placed in a temperature and humidity controlled environment. The temperature is maintained at about 23° C. and the humidity is maintained at about 100 percent relative humidity. The samples are tested for AUL value at various points throughout a 20-day aging study. The results are set forth in Table 10.

TABLE 10

| Sample No. | AUL Value (g/g) | | | AUL Retention |
|---|---|---|---|---|
| | 0 days | 10 days | 20 days | |
| 144 | 23.1 | 19.7 | 17.3 | 75% |
| 145 | 20.2 | 20.5 | 19.8 | 98% |

Carboxymethyl cellulose is dissolved in distilled water to give 2 weight percent solutions and mixed using a commercial Hobart mixer run at low to medium speed. Samples 146 and 148 use Aqualon CMC-7H4F for the carboxymethyl cellulose. Sample 147 uses a carboxymethyl cellulose similar to the carboxymethyl cellulose prepared for further treatment to prepare the sample used in Table 9. Various amounts of trivalent cerium sulfate salt is added to the solutions. The solutions are dried at 80° C. overnight in a convection oven. After grinding and sieving, the samples are tested for AUL values. A post heat-treatment, at a temperature of 140° C. for various lengths of time, is used to additionally crosslink the samples. The samples are again tested for AUL values. The results are set forth in Table 11.

TABLE 11

| Sample No. | Wt. Ratio CMC/Ce$_2$(SO$_4$)$_3$ | Initial AUL (g/g) at various curing times (min.) | | | | | | | | | |
|---|---|---|---|---|---|---|---|---|---|---|---|
| | | 0 | 10 | 20 | 30 | 40 | 50 | 60 | 70 | 80 | 100 |
| 146 | 100/1 | — | 11.7 | 18.7 | 22.7 | 23.2 | 22.3 | 21.7 | — | 16.4 | 17.3 |
| 147 | 100/2 | 14.1 | 22.7 | 24.0 | 25.2 | 22.5 | 23.3 | 22.1 | 20.5 | — | — |
| 148 | 100/3 | — | 9.95 | 18.5 | 20.6 | 21.0 | 18.2 | 18.5 | — | 15.8 | 14.9 |

Sample No. 149 represents the material from Table 11 with a CMC/Ce$_2$(SO$_4$)$_3$ weight ratio of 100 to 1 wherein the CMC is post heat-treated at a temperature of 140° C. for 60 minutes. This sample is placed in a controlled environment at ambient conditions of about 23° C. and about 30 to about 60 percent relative humidity. The sample is tested for AUL value at various points throughout an 11-month aging study. The results are set forth in Table 12.

TABLE 12

| Sample No. | AUL Value (g/g) | | |
|---|---|---|---|
| | 0 days | 3 months | 11 months |
| 149 | 21.7 | 22.0 | 18.5 |

Sample No. 150 represents a carboxymethyl cellulose, Aqualon CMC-7H4F, with no crosslinking agent added. Sample No. 151 represents the material from Table 11 wherein the weight ratio of CMC/$Ce_{2(SO4)3}$ is 100/1 and wherein the CMC is post heat-treated at a temperature of 140° C. for 50 minutes. Sample No. 152 represents the material from Table 11 wherein the weight ratio of CMC/$Ce_2(SO_4)_3$ is 100/1 and wherein the CMC is post heat-treated at a temperature of 140° C. for 100 minutes. These samples are placed in a temperature and humidity controlled environment. The temperature is maintained at about 23° C. and the humidity is maintained at about 100 percent relative humidity. The samples are tested for AUL value at various points throughout an aging study. The results are set forth in Table 13.

TABLE 13

| Sample No. | AUL Value (g/g) | | |
|---|---|---|---|
| | 0 days | 10 days | 11 days |
| 150* | 20.9 | 9.8 | — |
| 151 | 22.3 | — | 11.1 |
| 152 | 17.3 | — | 16.9 |

*Not an example of the present invention

Example 7

Carboxymethyl cellulose (Aqualon CMC-7H4F) is dissolved in distilled water to give 3 weight percent solutions and mixed using a commercial Waring blender run at low speed. Various amounts of acids, based on the weight of CMC used, are added to the solutions. The solutions are spread out in teflon-coated trays and dried at 75° C. overnight in a convection oven. After grinding and sieving, the samples are tested for AUL values. The results are set forth in Table 14.

TABLE 14

| Sample | Additive | Initial Wt. % | Mole % | AUL (g/g) |
|---|---|---|---|---|
| 153* | none | 0 | 0 | 8.4 |
| 154 | glycolic acid | 1 | 2.87 | 8.3 |
| 155 | glycolic acid | 2.5 | 7.16 | 19.0 |
| 156 | glycolic acid | 5.0 | 14.32 | 14.2 |
| 157 | acetic acid | 1.97 | 7.16 | 10.7 |
| 158 | acetic acid | 3.94 | 14.32 | 16.7 |
| 159 | acetic acid | 5.91 | 21.48 | 17.0 |
| 160 | monochloroacetic acid | 0.6 | 1.38 | 19.7 |
| 161 | monochloroacetic acid | 1.2 | 2.76 | 15.1 |
| 162 | monochloroacetic acid | 3.1 | 7.16 | 8.7 |
| 163 | sodium chloroacetate | 0.5 | 0.93 | 15.1 |
| 164 | sodium chloroacetate | 1.0 | 1.87 | 15.4 |

TABLE 14-continued

| Sample | Additive | Initial Wt. % | Mole % | AUL (g/g) |
|---|---|---|---|---|
| 165 | sodium chloroacetate | 2.0 | 3.74 | 11.4 |
| 166 | HCl | 0.48 | 2.87 | 8.8 |
| 167 | HCl | 0.96 | 5.74 | 14.6 |
| 168 | HCl | 1.34 | 8.61 | 17.5 |
| 169 | HCl | 2.4 | 14.32 | 10.4 |

*Not an example of the present invention

Additional samples, using monochloroacetic acid (MCAA) as a crosslinking additive, are prepared using a similar process used to prepare the samples set forth in Table 14. These samples are placed in a temperature and humidity controlled environment. For Samples 170 and 171, the temperature is maintained at about 23° C. and the humidity is maintained at about 100 percent relative humidity. For Samples 172 and 173, the temperature is maintained at about 110° F. (about 43° C.) and the humidity is maintained at about 80 percent relative humidity. For Samples 174 and 175, the temperature is maintained at about 23° C. and the humidity is maintained at ambient conditions, between about 30 to about 60 percent relative humidity. The samples are tested for AUL value, at 0.3 psi, at various points throughout an aging study. The results are set forth in Table 15.

TABLE 15

| Sample No. | wt. ratio MCAA/CMC | AUL Value (g/g) | | | | | |
|---|---|---|---|---|---|---|---|
| | | 0 days | 7 days | 14 days | 33 days | 60 days | 108 days |
| 170 | 0.6/100 | 18.8 | 16.9 | 16.75 | 14.0 | 9.25 | — |
| 171 | 1.2/100 | 13.6 | 13.3 | 14.63 | 14.19 | — | — |
| 172 | 0.6/100 | 18.8 | — | — | 16.0 | 15.6 | — |
| 173 | 1.2/100 | 13.6 | — | — | 10.5 | 9.1 | — |
| 174 | 0.6/100 | 18.8 | — | — | — | — | 17.0 |
| 175 | 1.2/100 | 13.6 | — | — | — | — | 11.4 |

Various amounts of acetic acid are added to water to achieve a desired pH. Carboxymethyl cellulose (Aqualon CMC-7H4F) is dissolved in the acidified water to give 3 weight percent CMC solutions and mixed using a commercial Waring blender run at low speed. After the CMC is completely dissolved in the acidified water, the pH of the mixture is measured. This pH value is reported in Table 16. The solutions are spread out in teflon-coated trays, dried at 40° C. overnight in a convection oven, and then ground and sieved. A post heat-treatment, at various temperatures and for various lengths of time, is used to additionally crosslink the samples. These samples are placed in a temperature and humidity controlled environment. For Samples 176–180, Aqualon CMC-7H4F is used for the carboxymethylcellulose, the heat-treatment conditions used are 140° C. for 90 minutes, and the aging conditions used are that the temperature is maintained at about 23° C. and the humidity is maintained at ambient conditions, between about 30 to about 60 percent relative humidity. For Samples 181–182, Aqualon CMC-7HCF is used for the carboxymethylcellulose, the heat-treatment conditions used are 100° C. for 120 minutes for Sample 181 and 150° C. for 35 minutes for Sample 182, and the aging conditions used are that the temperature is maintained at about 23° C. and the humidity is maintained at ambient conditions, between about 30 to about 60 percent relative humidity.

TABLE 16

| Sample No. | pH | \multicolumn{9}{c}{AUL Value (g/g)} |
|---|---|---|---|---|---|---|---|---|---|---|
| | | 0 days | 15 days | 30 days | 45 days | 60 days | 90 days | 120 days | 150 days | 240 days |
| 176 | 6.8 | 14.2 | — | 14.2 | 14.4 | 14.4 | — | — | 16.4 | — |
| 177 | 6.9 | 16.1 | — | 16.3 | 16.5 | 17.1 | — | — | 18.1 | — |
| 178 | 7.2 | 18.1 | — | 17.9 | 18.1 | 17.3 | — | — | 16.1 | — |
| 179 | 7.4 | 19.7 | — | 19.4 | 19.0 | 18.2 | — | — | 15.6 | — |
| 180 | 7.6 | 21.3 | — | 19.0 | 18.9 | 17.4 | — | — | 9.5 | — |
| 181 | 6.0 | 22.1 | — | 21.3 | — | 19.8 | 19.0 | 16.8 | — | 15.7 |
| 182 | 7.6 | 22.3 | 16.5 | 11.8 | 7.6 | 7.7 | 6.8 | — | — | — |

Example 8

Carboxymethyl cellulose (Aqualon CMC-7H4F) is dissolved in distilled water to give 2 weight percent solutions and mixed using a commercial Hobart mixer run at low to medium speed. Various amounts of an amino acid, aspartic acid (AA), is added to the solutions. The solutions are dried at 80° C. overnight in a convection oven. After grinding and sieving, the samples are tested for AUL values at 0.3 psi. A post heat-treatment, at a temperature of 140° C. for various lengths of time, is used to additionally crosslink the samples. The samples are again tested for AUL values at about 0.3 psi. The results are set forth in Table 17.

TABLE 17

| Sample | Weight Ratio AA:CMC | \multicolumn{7}{c}{AUL (g/g) at various curing times} |
|---|---|---|---|---|---|---|---|---|
| | | 0 min. | 5 min. | 10 min. | 15 min. | 20 min. | 25 min. | 30 min. |
| 183* | 0:100 | 7.6 | — | 24.0 | — | 24.7 | — | 24.6 |
| 184 | 0.5:100 | 9.84 | 8.34 | 14.21 | 18.89 | 19.11 | 18.10 | 18.44 |
| 185 | 1;100 | 8.40 | 13.30 | 20.2 | 17.73 | 15.58 | 14.58 | 14.05 |
| 186 | 1.5:100 | 9.36 | 12.47 | 16.28 | 16.39 | 16.23 | 15.29 | 13.53 |
| 187 | 2.5:100 | 18.21 | 13.09 | 9.54 | — | — | — | — |

*Not an example of the present invention.

Sample No. 188 represents the material from Table 17 wherein the weight ratio of aspartic acid/CMC is 2.5/100 and wherein the CMC is post heat-treated at a temperature of 110° C. for various lengths of time. The samples are tested for AUL value, at 0.3 psi, after the heat-treatment. The results are set forth in Table 18.

TABLE 18

| Sample | \multicolumn{7}{c}{AUL (g/g) at various curing times} |
|---|---|---|---|---|---|---|---|
| | 0 min. | 5 min. | 10 min. | 15 min. | 20 min. | 25 min. | 30 min. |
| 188 | 18.21 | 18.09 | 18.43 | 18.15 | 17.90 | 16.84 | 16.22 |

Sample No. 189 represents the material from Table 18 wherein the CMC is post heat-treated at a temperature of 110° C. for 10 minutes. Sample No. 190 represents the material from Table 18 wherein the CMC is post heat-treated at a temperature of 110° C. for 15 minutes. Sample No. 191 represents the material from Table 18 wherein the CMC is post heat-treated at a temperature of 110° C. for 20 minutes. Sample No. 192 represents a control material wherein no aspartic acid is added to the CMC and wherein the CMC is post heat-treated at a temperature of 140° C. for 30 minutes. These samples are placed in a temperature and humidity controlled environment. The temperature is maintained at about 23° C. and the humidity is maintained at about 100 percent relative humidity. The samples are tested for AUL value, at 0.3 psi, at various points throughout an aging study.

The results are set forth in Table 19.

TABLE 19

| Sample No. | \multicolumn{3}{c}{AUL Value (g/g)} |
|---|---|---|---|
| | 0 days | 5 days | 12 days |
| 189 | 18.43 | — | 15.51 |
| 190 | 18.15 | — | 16.20 |
| 191 | 17.90 | — | 15.21 |
| 192* | 24.4 | 12.0 | — |

*Not an example of the present invention.

Example 9

Carboxymethyl cellulose (Aqualon CMC-7H4F) is dissolved in distilled water to give 2 weight percent solutions and mixed using a stainless steel mixer with agitator. Various amounts of citric acid (CA), as a crosslinking agent, and sodium hypophosphite (SHP), as a crosslinking catalyst, are added to the solutions. The solutions are mixed well at 25° C., poured into teflon-lined trays, and dried at 95° C. for 16 hours in a convection oven. After grinding and sieving to a 300 to 600 micron size fraction, the samples are tested for AUL values at 0.3 psi. The results are set forth in Table 20.

TABLE 20

| Sample No. | CA:SHP:CMC wt. ratio | AUL g/g |
|---|---|---|
| 193* | 0:0:100 | 6.9 |
| 194 | 0.3:0.15:100 | 18.5 |
| 195 | 0.5:0.25:100 | 19.1 |
| 196 | 0.6:0.30:100 | 21.3 |
| 197 | 0.7:0.35:100 | 17.5 |
| 198 | 0:8:0.40:100 | 14.6 |
| 199 | 1.0:0.50:100 | 13.6 |
| 200 | 1.5:0.75:100 | 12.3 |
| 201 | 0.3:0:100 | 21.1 |
| 202 | 0.6:0:100 | 18.3 |
| 203 | 1.0:0:100 | 16.7 |

*Not an example of the present invention.

Samples 196, 197, and 199 are also placed in a temperature and humidity controlled environment. The temperature is maintained at about 25° C. and the humidity is maintained at about 100 percent relative humidity. The samples are tested for AUL value, at 0.3 psi, at various points throughout an aging study. The results are set forth in Table 21.

TABLE 21

| Sample No. | AUL Value (g/g) | | |
|---|---|---|---|
| | 0 days | 12 days | 20 days |
| 196 | 21.3 | 18.6 | 18.7 |
| 197 | 17.5 | 20.1 | 19.6 |
| 199 | 13.6 | 15.5 | 18.6 |

Example 10

A general slurry process synthetic scheme is used to prepare samples of carboxymethyl cellulose from cellulose and is generally described as follows: 15 grams of cellulose is immersed in 400 milliliters of isopropanol in a reaction kettle equipped with a mechanical stirrer, an inert gas inlet, and a temperature control probe. Thirty-five milliliters of water (containing the desired amount of alkali) is then added. The slurry is stirred for half an hour at room temperature (about 23° C.) before adding the appropriate amount of chloroacetic acid (CAA). The reaction is carried out for three hours at 60° C. The slurry is then filtered, the product washed twice with a 70:30 volume-percent mixture (400 ml) of methanol and water, washed once with 400 ml of methanol, and allowed to dry. The recovered carboxymethyl cellulose is then dispersed in water, dried at 30° C., and ground into granules. The particle size fraction between 300 and 600 microns is collected for absorbency testing. The degree of substitution (D.S.) of the carboxymethyl cellulose products is measured by $^1$H-NMR spectroscopy. The morphological features of dispersions of the carboxymethyl cellulose products is observed by cross-polarized optical microscopy and X-ray diffraction. The AUL tests are performed at 0.3 psi. The aging tests are accomplished by placing the granular samples into a chamber saturated with water vapor (100 percent relative humidity) at room temperature (about 24° C). At certain intervals of aging time, the samples are taken out of the chamber and dried in ambient conditions for two days before doing the absorbency tests. The unused samples are replaced in the chamber for continued aging.

For the following samples, various cellulose pulps or carboxymethyl celluloses are used, as is indicated in Table 22–24. Aqualon's Cellulose Gum CMC-7H4F is indicated by the designation CMC-7H4F. A cellulose pulp commercially available from ITT Rayonier Corp. under the trade designation Porosanier-J, is a southern pine wood pulp having an intrinsic viscosity of about 8.4 deciliters/g and having an alpha cellulose content of about 98.7 percent, is indicated by the designation ITT. A cellulose pulp commercially available from Southern Cellulose Products, Inc. under the trade designation Grade 1050, is a cotton linters pulp having an alpha cellulose content of about 99.2 percent, is indicated by the designation SC. A cellulose pulp prepared using a Kraft process without cold caustic treatment after bleaching, having a viscosity of about 15.3 centipoise and an alpha cellulose content of about 94.6 percent, is indicated by the designation CR#8. A cellulose pulp prepared using a Kraft process from a southern softwood chips, wherein sodium hydroxide is used for a cold caustic treatment after bleaching, having a viscosity of about 19.8 centipoise and a degree of polymerization (number average) of about 1477 is indicated by the designation CR#10. A cellulose pulp prepared using a Kraft process from a southern softwood, wherein sodium hydroxide is used for a cold caustic treatment after bleaching, having a viscosity of about 16.6 centipoise and a degree of polymerization (number average) of about 1368 is indicated by the designation CR#11. A cellulose pulp prepared using a Kraft process from aspen chips without cold caustic treatment after bleaching, having a viscosity of about 41.2 centipoise and a degree of polymerization (number average) of about 1997 is indicated by the designation CR#18. The cellulose pulp used to prepare Sample 143 in Table 9 is indicated by the designation CR#21.

For comparison, water-soluble carboxymethyl cellulose samples are synthesized. Table 22 provides the reaction conditions and the absorbency values of the prepared samples. The samples are all soluble in the testing saline solution and the AUL values are for samples aged at ambient temperature (about 24° C.) and at about 100 percent relative humidity.

TABLE 22

| Sample | Cellulose | NaOH:CAA Molar Ratio | CAA:Cellulose Molar Ratio | DS | AUL (g/g) | | |
|---|---|---|---|---|---|---|---|
| | | | | | 0 days | 12 days | 20 days |
| 204* | CMC-7H4F | — | — | 0.7–0.8 | 7.3 | 7.1 | 6.5 |
| 205* | CR#11 | 2.2:1 | 0.75:1 | 0.78 | 7.1 | 7.4 | 8.9 |
| 206* | ITT | 2.0:1 | 1.0:1 | 0.96 | 6.6 | 8.6 | 8.8 |
| 207* | ITT | 2.2:1 | 1.0:1 | 1.0 | 8.8 | 7.6 | 7.1 |

*Not examples of the present invention

Samples are prepared using potassium hydroxide (KOH) as the alkali. Table 23 provides the reaction conditions and the absorbency values of the prepared samples. The samples are all translucent or fibrous when dispersed in water.

TABLE 23

| Sample | Cellulose | KOH:CAA Molar Ratio | CAA:Cellulose Molar Ratio | DS | AUL (g/g) | | |
|---|---|---|---|---|---|---|---|
| | | | | | 0 days | 12 days | 20 days |
| 208 | CR#8 | 2.0:1 | 2.0:1 | 0.92 | 14.5 | — | — |
| 209 | CR#10 | 2.0:1 | 1.0:1 | 0.76 | 14.3 | — | — |
| 210 | CR#10 | 2.0:1 | 1.5:1 | 1.13 | 14.0 | — | — |

TABLE 23-continued

| Sample | Cellulose | KOH:CAA Molar Ratio | CAA:Cellulose Molar Ratio | DS | AUL (g/g) 0 days | 12 days | 20 days |
|---|---|---|---|---|---|---|---|
| 211 | ITT | 2.2:1 | 0.75:1 | — | 13.3 | 14.4 | 14.9 |
| 212 | ITT | 2.2:1 | 1.0:1 | — | 17.3 | 16.9 | 18.4 |

As can be seen, for example, by comparing Samples 207 and 212, the use of potassium hydroxide as compared to using sodium hydroxide results in a carboxymethyl cellulose that exhibits both a high initial Absorbency Under Load value and exhibits aging stability.

Sample No. 213 and 214 are prepared using a less than stoichiometric amount of alkali, as indicated by the molar ratio of alkali to chloroacetic acid used being less than 2:1. Sample No. 215 to 222 are prepared using less modifying agent, as indicated by the molar ratio of chloroacetic acid to cellulose used being less than 1:1.

Table 24 provides the reaction conditions and the absorbency values of the prepared samples.

TABLE 24

| Sample | Cellulose | NaOH:CAA Molar Ratio | CAA:Cellulose Molar Ratio | DS | AUL (g/g) 0 days | 12 days | 20 days |
|---|---|---|---|---|---|---|---|
| 213 | ITT | 1.8:1 | 0.75:1 | 0.65 | 12.6 | — | — |
| 214 | ITT | 1.8:1 | 1.00:1 | 0.84 | 17.2 | — | — |
| 215 | ITT | 2:1 | 0.75:1 | 0.76 | 17.1 | — | — |
| 216 | ITT | 2.2:1 | 0.60:1 | — | 17.2 | — | — |
| 217 | ITT | 2.5:1 | 0.50:1 | — | 16.2 | — | — |
| 218 | SC | 2.2:1 | 0.60:1 | — | 16.1 | — | — |
| 219 | SC | 2.2:1 | 0.40:1 | — | 11.8 | — | — |
| 220 | CR#21 | 2.2:1 | 0.50:1 | — | 19.2 | 18.7 | 18.9 |
| 221 | CR#21 | 2.2:1 | 0.40:1 | — | 13.7 | — | — |
| 222 | CR#18 | 2.2:1 | 0.50:1 | — | 17.0 | — | — |

Samples 208 and 214–217 are also placed in a temperature and humidity controlled environment. The temperature is maintained at about 23° C. and the humidity is maintained at about 100 percent relative humidity. The samples are tested for AUL value, at 0.3 psi, at various points throughout an aging study. The results are set forth in Table 25.

TABLE 25

| Sample No. | AUL Value (g/g) 0 days | 12 days | 40 days | 52 days | 77 days |
|---|---|---|---|---|---|
| 208 | 14.5 | 14.5 | 15.1 | 14.8 | 14.8 |
| 214 | 17.2 | 14.6 | 14.3 | — | — |
| 215 | 17.1 | 15.0 | 17.4 | — | — |
| 216 | 17.2 | 15.8 | 16.6 | — | — |
| 217 | 16.2 | 14.8 | 15.6 | — | — |

Example 11

Carboxymethyl cellulose (Aqualon CMC-7H4F) is dissolved in distilled water to give 2 weight percent solutions and mixed using a commercial Hobart mixer run at low to medium speed. The solutions are dried at 80° C. overnight in a convection oven and ground and sieved. A post heat-treatment, at a temperature of 226° C. for various lengths of time, is used to crosslink the samples. These samples are placed in a temperature and humidity controlled environment. For Samples 223–228, the temperature is maintained at about 37.8° C. and the humidity is maintained at about 80 percent relative humidity. For Samples 229–234, the temperature is maintained at about 25° C. and the humidity is maintained at about 100 percent relative humidity. The samples are tested for AUL value, at about 0.3 psi, at various points throughout an aging study. The results are set forth in Table 26.

TABLE 26

| Sample # | Heat-Treatment Time (sec) | AUL Value (g/g) 0 days | 10 days | 20 days |
|---|---|---|---|---|
| 223 | 40 | 22.9 | 12.8 | 9.57 |
| 224 | 50 | 22.6 | 19.8 | 11.5 |
| 225 | 60 | 23.6 | 19.7 | 18.4 |
| 226 | 70 | 18.4 | 22.3 | 22.1 |
| 227 | 80 | 17.2 | 23.5 | 21.7 |
| 228 | 90 | 15.1 | 20.3 | 21.9 |
| 229 | 40 | 22.9 | 12.8 | 10.9 |
| 230 | 50 | 22.6 | 16.8 | 11.1 |
| 231 | 60 | 23.6 | 20.7 | 12.8 |
| 232 | 70 | 18.4 | 22.2 | 20.7 |
| 233 | 80 | 17.2 | 24.1 | 21.6 |
| 234 | 90 | 15.1 | 22.2 | 22.1 |

While the present invention has been described in terms of the specific embodiments described above, numerous equivalent changes and modifications will be clear to those skilled in the art. Accordingly, the specific examples set forth above are not intended to limit, in any manner, the scope of the invention as set forth in the appended claims.

What is claimed is:

1. A method for producing a water-swellable, water-insoluble carboxyalkyl polysaccharide, the method comprising the following steps:

forming a homogeneous mixture comprising a water-soluble carboxyalkyl polysaccharide, water, and a crosslinking agent, wherein the water-soluble carboxyalkyl polysaccharide dissolves into the water;

recovering said carboxyalkyl polysaccharide and said crosslinking agent from said mixture; and heat-treating said recovered carboxyalkyl polysaccharide and said crosslinking agent at a temperature above about 50° C. for a time effective to crosslink said carboxyalkyl polysaccharide to render said carboxyalkyl polysaccharide water swellable and water insoluble, wherein the water-swellable, water-insoluble carboxyalkyl polysaccharide exhibits an initial Absorbency Under Load value of at least 17 and retains at least about 50 percent of the initial Absorbency Under Load value after aging for about 60 days at about 24° C. and at least about 30 percent relative humidity.

2. The method according to claim 1 wherein the carboxyalkyl polysaccharide is prepared from a polysaccharide selected from the group consisting of cellulose, starch, guar, carrageenan, agar, gellan gum, chitin, chitosan, and mixtures thereof.

3. The method according to claim 1 wherein the carboxyalkyl polysaccharide is a carboxyalkyl cellulose.

4. The method according to claim 1 wherein the carboxyalkyl polysaccharide is a carboxymethyl polysaccharide.

5. The method according to claim 4 wherein the carboxymethyl polysaccharide is carboxymethyl cellulose.

6. The method according to claim 1 wherein the water-swellable, water-insoluble carboxyalkyl polysaccharide exhibits an initial Absorbency Under Load value of at least about 20.

7. The method according to claim 1 wherein said recovered carboxyalkyl polysaccharide and crosslinking agent are heat-treated at a temperature of from about 100° C. to about 200° C. for a time of from about 1 minute to about 600 minutes.

8. The method according to claim 1 wherein said mixture, comprising said water-soluble carboxyalkyl polysaccharide, water, and a crosslinking agent, has a pH between about 4 to about 9.

9. The method according to claim 1 wherein the heat-treated carboxyalkyl polysaccharide has an initial Absorbency Under Load value at least about 10 percent greater than an otherwise identical carboxyalkyl polysaccharide prepared without a crosslinking agent.

10. The method according to claim 9 wherein the heat-treated carboxyalkyl polysaccharide has an initial Absorbency Under Load value at least about 20 percent greater than an otherwise identical carboxyalkyl polysaccharide prepared without a crosslinking agent.

11. The method according to claim 1 wherein the water-swellable, water-insoluble carboxyalkyl polysaccharide retains at least about 70 percent of the initial Absorbency Under Load value after aging for about 60 days at about 24° C. and at least about 30 percent relative humidity.

12. The method according to claim 1 wherein the water-swellable, water-insoluble carboxyalkyl polysaccharide retains at least about 50 percent of the initial Absorbency Under Load value after aging for about 60 days at about 24° C. and at about 100 percent relative humidity.

13. The method according to claim 1 wherein said carboxyalkyl polysaccharide and said crosslinking agent are recovered by evaporative drying.

14. The method according to claim 1 wherein said carboxyalkyl polysaccharide and said crosslinking agent are recovered by precipitation.

15. The method according to claim 1 wherein the crosslinking agent is selected from the group consisting of an organic compound comprising at least two functional groups capable of reacting with a carboxyl, amino, or hydroxyl group of a carboxyalkyl polysaccharide or a metal ion with more than two positive charges.

16. The method according to claim 15 wherein said crosslinking agent is selected from the group consisting of diamines, polyamines, diols, polyols and mixtures thereof.

17. The method according to claim 6 wherein the crosslinking agent is selected from the group consisting of chitosan glutamate, type A gelatin, diethylenetriamine, ethylene glycol, butylene glycol, polyvinyl alcohol, hyaluronic acid, polyethylene imine, and mixtures thereof.

18. The method according to claim 15 wherein said crosslinking agent is selected from the group consisting of chloroacetic acid and sodium chloroacetate and mixtures thereof.

19. The method according to claim 15 wherein said crosslinking agent comprises a metal ion selected from the group consisting of $Al^{3+}$, $Fe^{3+}$, $Ce^{3+}$, $Ti^{4+}$, $Zr^{4+}$, and $Ce^{4+}$.

20. The method according to claim 19 wherein said crosslinking agent is selected from the group consisting of $AlCl_3$, $FeCl_3$, $Ce_2(SO_4)_3$, $Zr(NH_4)_4(CO_3)_4$, $Ce(NH_4)_4(SO_4)_4 \cdot 2H_2O$, and mixtures thereof.

21. The method according to claim 1 wherein the water-swellable, water-insoluble carboxymethyl cellulose retains at least about 50 percent of the initial Absorbency Under Load value after aging for about 60 days at about 24° C. and at about 100 percent relative humidity.

22. A method for producing a water-swellable, water-insoluble carboxymethyl cellulose, the method comprising the following steps:

forming a homogeneous mixture comprising a water-soluble carboxymethyl cellulose, water, and a crosslinking agent selected from the group consisting of organic compounds comprising at least two functional groups capable of reacting with a carboxyl or hydroxyl group of a carboxyalkyl polysaccharide and a metal ion having more than 2 positive charges, wherein the water-soluble carboxyalkyl polysaccharide dissolves into the water;

recovering said carboxymethyl cellulose and said crosslinking agent from said mixture; and heat-treating said recovered carboxymethyl cellulose and crosslinking agent at a temperature above about 100° C. for a time effective to crosslink said carboxymethyl cellulose to render said carboxymethyl cellulose water swellable and water insoluble wherein said heat-treated carboxymethyl cellulose has an initial Absorbency Under Load value of at least 17 and retains at least about 50 percent of the initial Absorbency Under Load value after aging for about 60 days at about 24° C. and at least about 30 percent relative humidity.

23. The method according to claim 22 wherein said crosslinking agent is selected from the group consisting of chitosan glutamate, type A gelatin, diethylenetriamine, ethylene glycol, butylene glycol, polyvinyl alcohol, hyaluronic acid, polyethylene imine, chloroacetic acid, sodium chloroacetate, $AlCl_3$, $FeCl_3$, $Ce_2(SO_4)_3$, $Zr(NH_4)_4(CO_3)_4$, $Ce(NH_4)_4(SO_4)_4 \cdot 2H_2O$, and mixtures thereof.

24. The method according to claim 22 wherein said carboxymethyl cellulose and said crosslinking agent are heat-treated at a temperature of from about 100° C. to about 200° C. for a time of from about 1 minute to about 600 minutes.

25. The method according to claim 22 wherein said carboxymethyl cellulose and said crosslinking agent are recovered by evaporative drying.

26. The method according to claim 22 wherein the water-swellable, water-insoluble carboxymethyl cellulose retains at least about 70 percent of the initial Absorbency Under Load value after aging for about 60 days at about 24° C. and at least about 30 percent relative humidity.

27. A method for producing a water-swellable, water-insoluble carboxyalkyl polysaccharide, the method comprising the following steps:

forming a homogeneous mixture comprising a water-soluble carboxyalkyl polysaccharide and water, wherein the water-soluble carboxyalkyl polysaccharide dissolves into the water;

recovering said carboxyalkyl polysaccharide from said mixture; and heat-treating said recovered carboxyalkyl polysaccharide at a temperature between about 200° C. and about 250° C. for an amount of time between about 50 to about 90 seconds, wherein said heat-treating is effective to crosslink said carboxyalkyl polysaccharide to render said carboxyalkyl polysaccharide water swellable and water insoluble, wherein the water-swellable, water-insoluble carboxyalkyl polysaccharide exhibits an initial Absorbency Under Load value of at least 17 and retains at least about 50 percent of the initial Absorbency Under Load value after aging for about 60 days at about 24° C. and at least about 30 percent relative humidity.

28. The method according to claim 27 wherein the carboxyalkyl polysaccharide is prepared from a polysaccharide selected from the group consisting of cellulose, starch, guar, carrageenan, agar, gellan gum, chitin, chitosan, and mixtures thereof.

29. The method according to claim 28 wherein the carboxyalkyl polysaccharide is a carboxymethyl polysaccharide.

30. The method according to claim 29 wherein the carboxymethyl polysaccharide is carboxymethyl cellulose.

31. The method according to claim 27 wherein the carboxyalkyl polysaccharide is a carboxyalkyl cellulose.

32. The method according to claim 27 wherein said carboxyalkyl polysaccharide is recovered by evaporative drying.

33. The method according to claim 27 wherein said mixture, comprising said water-soluble carboxyalkyl polysaccharide and water has a pH between about 5 to about 9.

34. The method according to claim 27 wherein the water-swellable, water-insoluble carboxyalkyl polysaccharide exhibits an initial Absorbency Under Load value of at least about 20.

35. The method according to claim 27 wherein the water-swellable, water-insoluble carboxyalkyl polysaccharide retains at least about 70 percent of the initial Absorbency Under Load value after aging for about 60 days at about 24° C. and at least about 30 percent relative humidity.

36. The method according to claim 27 wherein the water-swellable, water-insoluble carboxyalkyl polysaccharide retains at least about 50 percent of the initial Absorbency Under Load value after aging for about 60 days at about 24° C. and at about 100 percent relative humidity.

37. A method for producing a water-swellable, water-insoluble carboxyalkyl polysaccharide, the method comprising the following steps:

forming a homogeneous mixture comprising a water-soluble carboxyalkyl polysaccharide and water, wherein the water-soluble carboxyalkyl polysaccharide dissolves into the water;

adding to the homogeneous mixture a solution comprising a crosslinking agent, comprising an aluminum ion, dissolved in water; and recovering said carboxyalkyl polysaccharide and said crosslinking agent from said mixture, wherein the water-swellable, water-insoluble carboxyalkyl polysaccharide exhibits an initial Absorbency Under Load value of at least 8 and retains at least about 50 percent of the initial Absorbency Under Load value after aging for about 60 days at about 24° C. and at least about 30 percent relative humidity.

38. The method according to claim 37 wherein the carboxyalkyl polysaccharide is prepared from a polysaccharide selected from the group consisting of cellulose, starch, guar, carrageenan, agar, gellan gum, chitin, chitosan, and mixtures thereof.

39. The method according to claim 37 wherein the carboxyalkyl polysaccharide is a carboxyalkyl cellulose.

40. The method according to claim 37 wherein the carboxyalkyl polysaccharide is a carboxymethyl polysaccharide.

41. The method according to claim 40 wherein the carboxymethyl polysaccharide is carboxymethyl cellulose.

42. The method according to claim 37 wherein said carboxyalkyl polysaccharide and said crosslinking agent are recovered by evaporative drying.

43. The method according to claim 37 wherein the water-swellable, water-insoluble carboxyalkyl polysaccharide exhibits an initial Absorbency Under Load value of at least about 20.

44. The method according to claim 37 wherein the water-swellable, water-insoluble carboxyalkyl polysaccharide retains at least about 70 percent of the initial Absorbency Under Load value after aging for about 60 days at about 24° C. and at least about 30 percent relative humidity.

45. The method according to claim 37 wherein the water-swellable, water-insoluble carboxyalkyl polysaccharide retains at least about 50 percent of the initial Absorbency Under Load value after aging for about 60 days at about 24° C. and at about 100 percent relative humidity.

46. A method for producing a water-swellable, water-insoluble carboxyalkyl polysaccharide comprising:

a. preparing a reaction dispersion comprising a solvent and a polysaccharide comprising an original crystalline structure;

b. adding a carboxyalkylating reagent to the reaction dispersion at conditions effective to allow the carboxyalkylating reagent to react with the polysaccharide to prepare a water-insoluble, water-dispersible carboxyalkyl polysaccharide, wherein the carboxyalkyl polysaccharide comprises an amount of the original crystalline structure of the polysaccharide and a non-crystalline structure;

c. recovering the water-insoluble, water-dispersible carboxyalkyl polysaccharide from the reaction dispersion;

d. preparing a mixture comprising the recovered water-insoluble, water-dispersible carboxyalkyl polysaccharide and water, wherein the carboxyalkyl polysaccharide is dispersed in the water and the non-crystalline structure of the carboxyalkyl polysaccharide dissolves into the water; and e. recovering the carboxyalkyl polysaccharide from the mixture, wherein the carboxyalkyl polysaccharide comprises an amount of the original crystalline structure of the polysaccharide to be effective to result in a water-swellable, water-insoluble carboxyalkyl polysaccharide exhibiting an initial Absorbency Under Load value of at least 17 and retaining at least about 50 percent of the initial Absorbency Under Load value after aging for about 60 days at about 24° C. and at least about 30 percent relative humidity.

47. The method according to claim 46 wherein the carboxyalkyl polysaccharide is prepared from a polysaccharide selected from the group consisting of cellulose, chitin, and mixtures thereof.

48. The method according to claim 46 wherein the carboxyalkyl polysaccharide is a carboxyalkyl cellulose.

49. The method according to claim 46 wherein the carboxyalkyl polysaccharide is a carboxymethyl polysaccharide.

50. The method according to claim 49 wherein the carboxymethyl polysaccharide is carboxymethyl cellulose.

51. The method according to claim 46 wherein said carboxyalkyl polysaccharide is recovered from the mixture by evaporative drying.

52. The method according to claim 46 wherein the water-swellable, water-insoluble carboxyalkyl polysaccharide exhibits an initial Absorbency Under Load value of at least about 20.

53. The method according to claim 46 wherein the water-swellable, water-insoluble carboxyalkyl polysaccharide retains at least about 70 percent of the initial Absorbency Under Load value after aging for about 60 days at about 24° C. and at least about 30 percent relative humidity.

54. The method according to claim 46 wherein the water-swellable, water-insoluble carboxyalkyl polysaccharide retains at least about 50 percent of the initial Absorbency Under Load value after aging for about 60 days at about 24° C. and at about 100 percent relative humidity.

55. The method according to claim 46 wherein potassium hydroxide is used as an alkali to prepare the carboxyalkyl polysaccharide.

56. The method according to claim 46 wherein a less than stoichiometric ratio of an alkali to the carboxyalkylating reagent is used to prepare the carboxyalkyl polysaccharide.

57. The method according to claim 56 wherein the ratio of the alkali to the carboxyalkylating reagent is less than about 2 to 1.

58. The method according to claim 46 wherein a reactant molar ratio of the carboxyalkylating reagent to the polysaccharide is less than 1 to 1.

59. The method according to claim 56 wherein the carboxyalkylating reagent is chloroacetic acid and the polysaccharide is cellulose.

60. A method for producing a water-swellable, water-insoluble carboxyalkyl polysaccharide comprising:

a. preparing a mixture comprising a water-insoluble, water-dispersible carboxyalkyl polysaccharide, wherein the carboxyalkyl polysaccharide comprises a crystalline structure and a non-crystalline structure, and water, wherein the carboxyalkyl polysaccharide is dispersed in the water and the non-crystalline structure of the carboxyalkyl polysaccharide dissolves into the water, and b. recovering the carboxyalkyl polysaccharide from the mixture to result in a water-swellable, water-insoluble carboxyalkyl polysaccharide exhibiting an initial Absorbency Under Load value of at least 17 and retaining at least about 50 percent of the initial Absorbency Under Load value after aging for about 60 days at about 24° C. and at least about 30 percent relative humidity.

61. The method according to claim 60 wherein the carboxyalkyl polysaccharide is prepared from a polysaccharide selected from the group consisting of cellulose, chitin, and mixtures thereof.

62. The method according to claim 60 wherein the carboxyalkyl polysaccharide is a carboxyalkyl cellulose.

63. The method according to claim 60 wherein the carboxyalkyl polysaccharide is a carboxymethyl polysaccharide.

64. The method according to claim 63 wherein the carboxymethyl polysaccharide is carboxymethyl cellulose.

65. The method according to claim 60 wherein said carboxyalkyl polysaccharide is recovered from the mixture by evaporative drying.

66. The method according to claim 60 wherein the water-swellable, water-insoluble carboxyalkyl polysaccharide exhibits an initial Absorbency Under Load value of at least about 20.

67. The method according to claim 60 wherein the water-swellable, water-insoluble carboxyalkyl polysaccharide retains at least about 70 percent of the initial Absorbency Under Load value after aging for about 60 days at about 24° C. and at least about 30 percent relative humidity.

68. The method according to claim 60 wherein the water-swellable, water-insoluble carboxyalkyl polysaccharide retains at least about 50 percent of the initial Absorbency Under Load value after aging for about 60 days at about 24° C. and at about 100 percent relative humidity.

* * * * *